US007723299B2

(12) United States Patent
Lee et al.

(10) Patent No.: US 7,723,299 B2
(45) Date of Patent: May 25, 2010

(54) METHODS FOR TREATING RHEUMATOID ARTHRITIS USING A CTLA-4 FUSION PROTEIN

(75) Inventors: Sang-Kyou Lee, Seoul (KR); Seung-Kyou Lee, Kyeunggi-Do (KR); Je-Min Choi, Seoul (KR)

(73) Assignee: ForHumanTech. Co., Ltd. (KR)

( * ) Notice: Subject to any disclaimer, the term of this patent is extended or adjusted under 35 U.S.C. 154(b) by 388 days.

(21) Appl. No.: 11/592,227

(22) Filed: Nov. 3, 2006

(65) Prior Publication Data
US 2007/0105775 A1 May 10, 2007

Related U.S. Application Data

(60) Provisional application No. 60/733,183, filed on Nov. 4, 2005.

(51) Int. Cl.
*A61K 38/16* (2006.01)
*C07K 14/00* (2006.01)

(52) U.S. Cl. ......................... 514/12; 530/350
(58) Field of Classification Search ....................... None
See application file for complete search history.

(56) References Cited

U.S. PATENT DOCUMENTS

| | | | |
|---|---|---|---|
| 6,025,140 | A | 2/2000 | Langel et al. |
| 6,166,191 | A | 12/2000 | Randazzo |
| 6,251,599 | B1 | 6/2001 | Chen et al. |
| 6,903,077 | B1 | 6/2005 | Heintz |
| 2003/0104622 | A1 | 6/2003 | Robbins et al. |
| 2003/0229202 | A1 | 12/2003 | Guo et al. |
| 2005/0014791 | A1 | 1/2005 | Tsantrizos et al. |
| 2005/0090646 | A1 | 4/2005 | Sullivan |
| 2005/0158373 | A1 | 7/2005 | Szeto et al. |
| 2006/0035815 | A1 | 2/2006 | Chen et al. |
| 2006/0041058 | A1 | 2/2006 | Yin et al. |
| 2006/0148060 | A1 | 7/2006 | Lee et al. |
| 2008/0132450 | A1 | 6/2008 | Lee et al. |
| 2009/0162857 | A1 | 6/2009 | Lee et al. |

FOREIGN PATENT DOCUMENTS

| | | |
|---|---|---|
| WO | WO 98/07858 A1 | 2/1998 |
| WO | WO 98/07860 A1 | 2/1998 |
| WO | WO 03/059940 A1 | 7/2003 |
| WO | WO 03059941 A1 * | 7/2003 |
| WO | WO 2004/044008 A1 | 5/2004 |
| WO | WO 2004/078933 A2 | 9/2004 |

OTHER PUBLICATIONS

Alkema, M.J., et al., "Identification of Bmi1-interacting proteins as constituents of a multimeric mammalian Polycomb complex," *Genes & Dev.* 11:226-240, Cold Spring Harbor Laboratory Press (1997).
Asemu, G., et al., "Identification of the changes in phospholipase C isozymes in ischemic-reperfused rat heart," *Arch. Biochem. Biophys.* 411:174-182, Elsevier Science (Mar. 2003).

Choi, H.S., et al., "Transduced Tat-α-Synuclein Protects against Oxidative Stress In vitro and In vivo," *J. Biochem. Mol. Biol.* 39:253-262, Korean Society for Biochemistry and Molecular Biology (May 2006).
Dent, M.R., et al., "Phospholipase C gene expression, protein content, and activities in cardiac hyperthrophy and heart failure due to volume overload," *Am. J. Physiol. Heart Circ. Physiol.* 287:H719-H727, The American Physiological Society (Apr. 2004).
Dietz, G.P.H., et al., "Inhibition of Neuronal Apoptosis in Vitro and in Vivo Using TAT-Mediated Protein Transduction," *Mol. Cell. Neurosci.* 21:29-37, Elsevier Science (Sep. 2002).
Gunster, M.J., et al., "Identification and Characterization of Interactions between the Vertebrate Polycomb-Group Protein BMI1 and Human Homologs of Polyhomeotic," *Mol. Cell. Biol* 17:2326-2335, American Society for Microbiology (1997).
Krief, S., et al., "Identification and Characterization of cvHSP," *J. Biol. Chem.* 274:36592-36600, The American Society for Biochemistry and Molecular Biology, Inc. (1999).
Kühnel, F., et al., "Protein Transduction Domains Fused to Virus Receptors Improve Cellular Virus Uptake and Enhance Oncolysis by Tumor-Specific Replicating Vectors," *J. Virol.* 78:13743-13754, American Society for Microbiology (Dec. 2004).
Lai, Y., et al., "Selectively increasing inducible heat shock protein 70 via TAT-protein transduction protects neurons from nitrosative stress and excitotoxicity," *J. Neurochem.* 94:360-366, International Society for Neurochemistry (Jul. 2005).
Lee, K-M., et al., "Molecular Basis of T Cell Inactivation by CTLA-4," *Science* 282:2263-2266, American Association for the Advancement of Science (1998).
Mangat, R., et al., "Inhibition of phospholipase C-$\gamma_1$ augments the decrease in cardiomyocyte viability by $H_2O_2$," *Am. J Physiol. Heart Circ. Physiol.* 291:H854-H860, The American Physiological Society (Feb. 2006).
Noguchi, H., et al., "A new cell-permeable peptide allows successful allogenic islet transplantation in mice," *Nat. Med.* 10:305-309, Nature Publishing Company (Feb. 2004).
Ohta, H., et al., "Structure and Chromosomal Localization of the *RAE28/HPH1* Gene, a Human Homologue of the *Polyhomeotic* Gene," *DNA Seq.* 11:61-73, (OPA) Overseas Publishers Association N.V. (2000).
Wheeler, D.S., et al., "Intracellular delivery of HSP70 using HIV-1 Tat protein transduction domain," *Biochem. Biophys. Res. Commun.* 301:54-59, Elsevier Science (Jan. 2003).
Yagisawa, H., "Nucleocytoplasmic Shuttling of Phospholipase C-$\delta_1$: A Link to $Ca^{2+}$," *J. Cell. Biochem.* 97:233-243, Wiley-Liss, Inc. (Oct. 2005).
International Search Report for International Application No. PCT/IB2006/003971, Korean Intellectual Property Office, Republic of Korea, mailed on Sep. 19, 2007.
International Search Report for International Application No. PCT/IB2007/003404, Korean Patent Office, Republic of Korea, mailed on May 2, 2008.

(Continued)

*Primary Examiner*—Ruixiang Li
(74) *Attorney, Agent, or Firm*—Sterne, Kessler, Goldstein & Fox P.L.L.C.

(57) ABSTRACT

The present invention relates to methods for delivery of fusion polypeptides into cells. Methods are provided for local delivery of fusion polypeptides, e.g., through the skin, eye and the airway, to prevent allergic inflammation, airway hyper-responsiveness and to block T cell activation. Methods for delivery of fusion polypeptides to suppress graft rejection are also provided.

11 Claims, 31 Drawing Sheets

OTHER PUBLICATIONS

International Search Report for International Application No. PCT/IB2007/004189, Korean Patent Office, Republic of Korea, mailed on Jun. 9, 2008.

Co-pending U.S. Appl. No. 11/878,431, inventors Lee, S-K., et al., filed Jul. 24, 2007 (Not Yet Published).

Becker-Hapak, M., et al., "TAT-Mediated Protein Transduction into Mammalian Cells," *Methods* 24:247-256, Academic Press (2001).

Buerger, C., et al., "Sequence-specific Peptide Aptamers, Interacting with the Intracellular Domain of the Epidermal Growth Factor Receptor, Interfere with Stat3 Activation and Inhibit the Growth of Tumor Cells," *J. Biol. Chem.* 278:37610-37621, The American Society for Biochemistry and Molecular Biology, Inc. (2003).

Chiu, Y.-L., et al., "Visualizing a Correlation between siRNA Localization, Cellular Uptake, and RNAi in Living Cells," *Chem. Bio.* 11:1165-1172, Elsevier Ltd. (Aug. 2004).

Choi, J.-M., et al., "Transduction of the cytoplasmic domain of CTLA-4 inhibits TcR-specific activation signals and prevents collagen-induced arthritis," *Proc. Natl. Acad. Sci. USA* 105:19875-19880, National Academy of Sciences (Dec. 2008).

Choi, J.-M., et al., "Intranasal delivery of the cytoplasmic domain of CTLA-4 using a novel protein transduction domain prevents allergic inflammation," *Nat. Med.* 12:574-579, Nature Publishing Group (May 2006).

Davidson, T.J., et al., "Highly Efficient Small Interfering RNA Delivery to Primary Mammalian Neurons Induces MicroRNA-Like Effects before mRNA Degradation," *J. Neurosci.* 24:10040-10046, Society for Neuroscience (Nov. 2004).

Dom, G., et al., "Cellular uptake of Antennapedia Penetratin peptides is a two-step process in which phase transfer precedes a tryptophan-dependent translocation," *Nucleic Acids Res.* 31:556-561, Oxford University Press (2003).

Eom, K.D., et al., "A Facile Synthesis and Physical Properties of Nano-Sized Dendritic α,ε-Poly(L-lysine)s for the Delivery of Nucleic Acids," *J. Nanosci. Nanotech.* 6:3532-3538, American Scientific Publishers (Nov. 2006).

Firestein, G.S., and Zvaifler, N.J., "How Important Are T Cells in Chronic Rheumatoid Synovitis? II. T Cell-Independent Mechanisms From Beginning to End," *Arthritis Rheum.* 46:298-308, American College of Rheumatology (2002).

Hashida, H., et al., "Fusion of HIV-1 Tat protein transduction domain to poly-lysine as a new DNA delivery tool," *Br. J. Cancer* 90:1252-1258, Cancer Research UK (Feb. 2004).

Hummel, K.M., et al., "Novel Strategies for the Therapy of Rheumatoid Arthritis," *Br. J. Rheumatol.* 36:265-267, British Society for Rheumatology (1997).

Lindgren, M., et al., "Cell-penetrating peptides," *Trends Pharmacol. Sci.* 21:99-103, Elsevier Science London (2000).

Masteller, E.L., et al., "Structural Analysis of CTLA-4 Function In Vivo," *J. Immunol.* 164:5319-5327, The American Association of Immunologists (2000).

Morris, M.C., et al., "A new peptide vector for efficient delivery of oligonucleotides into mammalian cells," *Nucleic Acids Res.* 25:2730-2736, Oxford University Press (1997).

Morris, M.C., et al., "A non-covalent peptide-based carrier for in vivo delivery of DNA mimics," *Nucleic Acids Res.* 35:e49, 1-10, Oxford University Press (Mar. 2007).

Moschos, S.A., et al., "Cell-penetrating-peptide-mediated siRNA lung delivery," *Biochem. Soc. Trans.* 35:807-810, Biochemical Society (Apr. 2007).

Muratovsk, A., and Eccles, M.R., "Conjugate for efficient delivery of short interfering RNA (siRNA) into mammalian cels," *FEBS Lett.* 558:63-68, Elsevier B.V. (Jan. 2004).

Rudolph, C., et al., "Oligomers of the Arginine-rich Motif of the HIV-1 TAT Protein Are Capable of Transferring Plasmid DNA into Cells," *J. Biol. Chem.* 278:11411-11418, The American Society for Biochemistry and Molecular Biology, Inc. (2003).

Segura, T., and Hubbell, J.A., "Synthesis and in Vitro Characterization of an ABC Triblock Copolymer for siRNA Delivery," *Bioconjugate Chem.* 18:736-745, American Chemical Society (Mar. 2007).

Siu, E., et al., "TCR subunit specifically of CTLA-4-mediated signaling," *J. Leukoc. Biol.* 74:1102-1107, Wiley-Liss (2003).

Takahashi, S., et al., "In vivo overexpression of CTLA-4 suppresses lymphoproliferative diseases and thymic negative selection," *Eur. J. Immunol.* 35:399-407, Wiley-VCH Verlag GmbH & Co. KGaA, Weinheim (Feb. 2005).

Thompson, C.B., and Allison, J.P., "The Emerging Role of CTLA-4 as an Immune Attenuator," *Immunity* 7:445-450, Cell Press (1997).

Torchilin, V.P., et al., "TAT peptide on the surface of liposomes affords their efficient intracellular delivery even at low temperature and in the presence of metabolic inhibitors," *Proc. Natl. Acad. Sci. USA* 98:8786-8791, National Academy of Sciences (2001).

Torchilin, V.P., et al., "Cell transfection in vitro and in vivo with nontoxic TAT peptide-liposome-DNA complexes," *Proc. Natl. Acad. Sci. USA* 100:1972-1977, National Academy of Sciences (2003).

Viehl, C.T., et al., "A Tat Fusion Protein-Based Tumor Vaccine for Breast Cancer," *Ann. Surg. Oncol.* 12:517-525, Society of Surgical Oncology, Inc. (Jul. 2005).

International Search Report for International Application No. PCT/KR03/00122, Korean Intellectual Property Office, Republic of Korean, mailed on May 14, 2003.

Supplementary European Search Report for EP Application No. EP 06 84 2388, Munich, Germany, search completed on Jun. 2, 2009, 8 pages.

Office Action mailed on Jul. 3, 2006 in U.S. Appl. No. 11/267,817, Lee, S.-K., et al., filed Nov. 7, 2005.

Office Action mailed on Aug. 10, 2007 in U.S. Appl. No. 11/267,817, Lee, S.-K., et al., filed Nov. 7, 2005.

Office Action mailed on Dec. 12, 2007 in U.S. Appl. No. 11/267,817, Lee, S.-K., et al., filed Nov. 7, 2005.

Office Action mailed on May 12, 2008 in U.S. Appl. No. 11/267,817, Lee, S.-K., et al., filed Nov. 7, 2005.

Office Action mailed on Jan. 7, 2009 in U.S. Appl. No. 11/267,817, Lee, S.-K., et al., filed Nov. 7, 2005.

Office Action mailed on Jul. 29, 2009 in U.S. Appl. No. 12/277,000, Lee, S.-K., et al., filed Nov. 24, 2008.

* cited by examiner (-) : β-gal
(+) : Mph-1-β-gal

Sequence of ctcCTLA-4

KMLKKRSPLTTGVYVKMPPTEPECEKQFQPYFIPIN

Sequence of ctcCTLA-4YF

KMLKKRSPLTTGVFVKMPPTEPECEKQFQPFFIPIN

Red : Mph-1-ctCTLA-4 10 μM
Green : Mph-1-ctCTLA-4 5 μM
Blue : Mph-1-ctCTLA-4 1 μM
Orange : only ctCTLA-4 10 μM Blue : 15 min
Green : 30 min
Red : 60 min
Yellow : 120 min
Orange : only ctCTLA-4 120 min Black : PBS (10% glycerol)
Green : only ctCTLA-4-EGFP 35 µg
Red : Mph-1-ctCTLA-4-EGFP 35 µg
Blue : Mph-1-ctCTLA-4-EGFP 18 µg

METHODS FOR TREATING RHEUMATOID ARTHRITIS USING A CTLA-4 FUSION PROTEIN

CROSS REFERENCE TO RELATED APPLICATIONS

This application claims the benefit of the filing date of U.S. Provisional Patent Application No. 60/733,183, filed Nov. 4, 2005, which is incorporated herein by reference in its entirety.

REFERENCE TO A SEQUENCE LISTING SUBMITTED ELECTRONICALLY VIA EFS-WEB

The content of the electronically submitted sequence listing (Name: substitute sequence listings.ascii.text, Size: 14 kilobytes; and Date of Creation: Aug. 26, 2009) filed with the application is incorporated by reference in its entirety.

STATEMENT REGARDING FEDERALLY-SPONSORED RESEARCH AND DEVELOPMENT

Not applicable.

BACKGROUND OF THE INVENTION

1. Field of the Invention

The present invention relates to methods for delivery of a biomolecule transduction complex (BTC), such as a fusion polypeptide, into cells. The biomolecule transduction complex (BTC) comprises a protein transduction domain (PTD) and a molecule of interest, such as a polypeptide.

2. Background Art

Generally, living cells are not permeable to macromolecules such as proteins and nucleic acids. The fact that only small-size molecules can permeate through the membrane of living cells at very low rates has restricted the research to develop drugs to cure, prevent, or diagnose diseases using macromolecules, such as, proteins and nucleic acids. Therefore, an effective method of transducing biologically active macromolecules into the cytosol and nucleus of living cells, without deleterious side effects, is needed.

Protein transduction domains (PTDs) have been used for delivery of biologically active molecules (Viehl C. T., et al., *Ann. Surg. Oncol.* 12:517-525 (2005); Noguchi H., et al., *Nat. Med.* 10:305-309 (2004); and Fu A. L., et al., *Neurosci. Lett.* 368:258-62 (2004)). However, no attempts have been made to use PTDs as a way of delivering a cytoplasmic domain of a receptor protein. Also, no attempts have been made for the intranasal delivery of a PTD with a biological molecule.

CTLA-4 (cytotoxic T lymphocyte antigen-4) is an activation-induced surface molecule on T cells and is essential for the negative regulation of T cell activation. It binds to B7-1 or -2 on antigen presenting cells (APC) with an affinity of 10- to 20-fold higher than that of CD28 which is a positive costimulatory molecule for T cell activation (Ngoc L. P., et al., *Curr. Opin. Allergy Clin. Immunol.* 5:161-166 (2005); Noel P. J., et al., *Adv. Exp. Med. Biol.* 406:209-217 (1996); and Perkins D., et al., *J. Immunol.* 156:4154-4159 (1996)).

The cytoplasmic domain of CTLA-4 containing Immunoreceptor Tyrosine-based Inhibitory Motif (ITIM) has been found to be 100% conserved among different species, suggesting that this domain is important for negative regulation of CTLA-4 on T cell activation by sequestering intracellular signaling molecules (Ravetch, J. V. & Lanier, L. L., *Science* 290:84-89 (2000); and Jay, C. U. & Jie, J., *Curr. Opin. Immunol.* 9:338-343 (1997)). Therefore, the cytoplasmic domain of CTLA-4 is an excellent molecular target for the development of immunotherapeutic drugs for asthma, autoimmune diseases and graft rejection. To date, attempts to deliver a receptor protein, in particular CTLA-4, into a cell using a PTD have been difficult. We have now shown a way to deliver CTLA-4 as a cargo for a PTD by fusing just the cytoplasmic domain of the receptor protein with a PTD. The cytoplasmic domain of CTLA-4 is specific to the activated T cells, so when used as a cargo protein for a PTD, it overcomes the lack of tissue specificity of the cationic PTDs which limited their in vivo utility.

BRIEF SUMMARY OF THE INVENTION

One object of this invention is to provide a method for inhibiting T cell activation in a vertebrate suffering from an autoimmune or inflammatory disease, comprising administering to the vertebrate a therapeutically effective amount of a fusion polypeptide comprising a protein transduction domain and a cytoplasmic domain of a receptor protein.

Another object of this invention is to provide a method for delivering a biomolecule transduction complex (BTC) to tracheal or lung cells, comprising intra-nasally administering the biomolecule transduction complex to a vertebrate. The biomolecule transduction complex comprises a protein transduction domain (PTD) and a molecule of interest.

Another preferred embodiment is the use of the cytoplasmic domain of CTLA-4 (SEQ ID NO:11) specific to the activated T cells as a cargo protein for PTD. Use of the PTD-ctCTLA-4 fusion protein overcomes the lack of tissue specificity of the cationic PTDs, which limits their in vivo utility.

Our invention enables the development of new therapeutic protein agents which comprise the protein transduction domains of certain proteins, such as Hph-1, with a high degree of cell or tissue specificity. Our invention also enables administration of the resultant fusion polypeptides via local administration routes, thereby minimizing or avoiding systemic side effects, such as behavioral abnormality, cytotoxicity, and immunogenicity.

BRIEF DESCRIPTION OF THE DRAWINGS/FIGURES

Figure 1A:
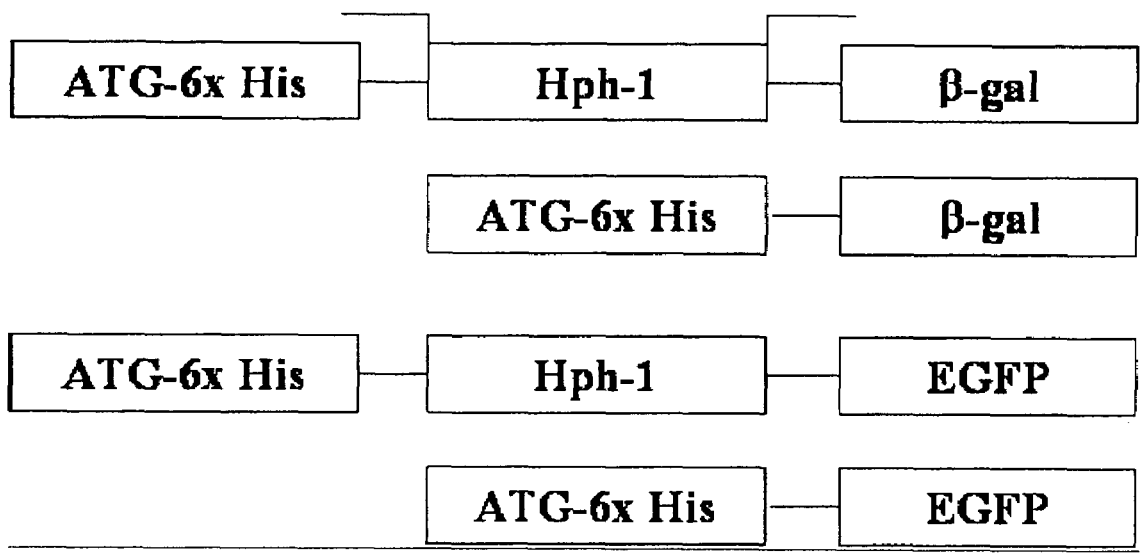
FIG. 1A shows the structure of the Hph-1-PTD β-gal or eGFP conjugated fusion proteins. Hph-1-PTD is an 11 amino acid protein transduction domain (YARVRRRGPRR) (SEQ ID NO:1) identified from human transcription factor Hph-1.
Figure 1B:
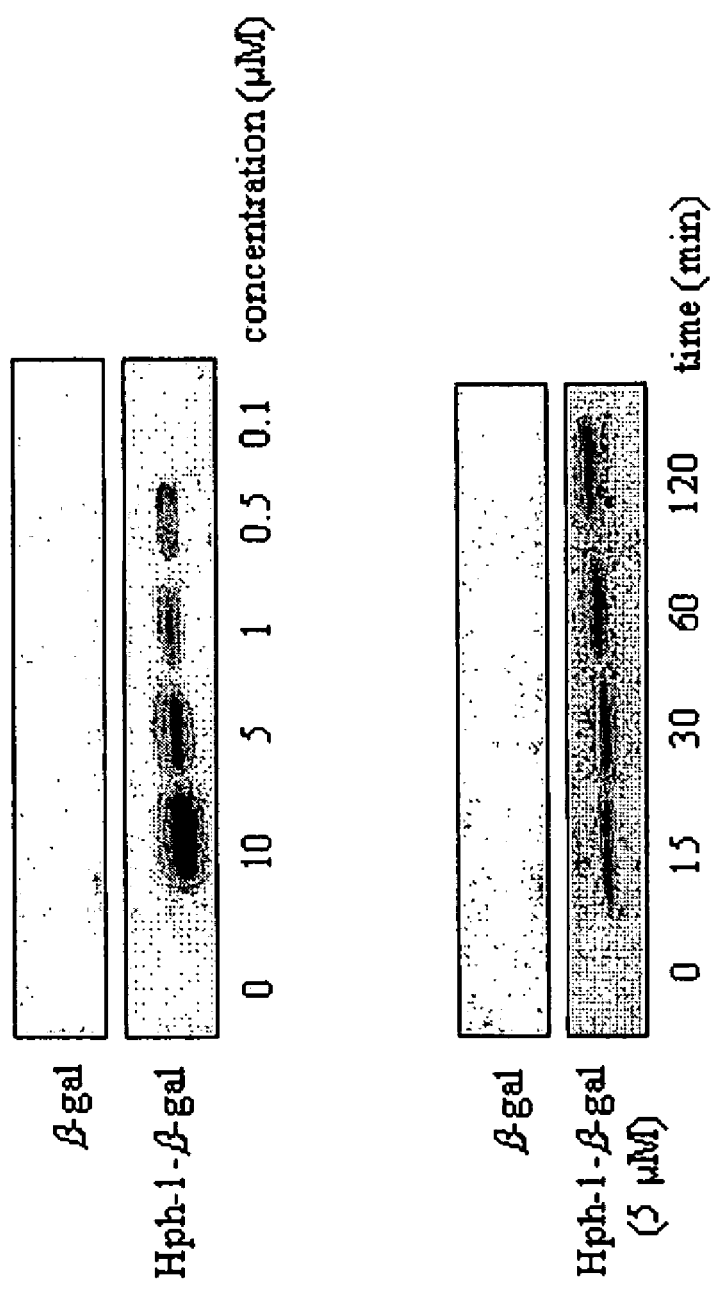
FIG. 1B are photographs of transduction activity and kinetics of the Mph-1-β-gal analyzed by Western blotting in cultured Jurkat (E6.1) T cells.
Figure 1C:
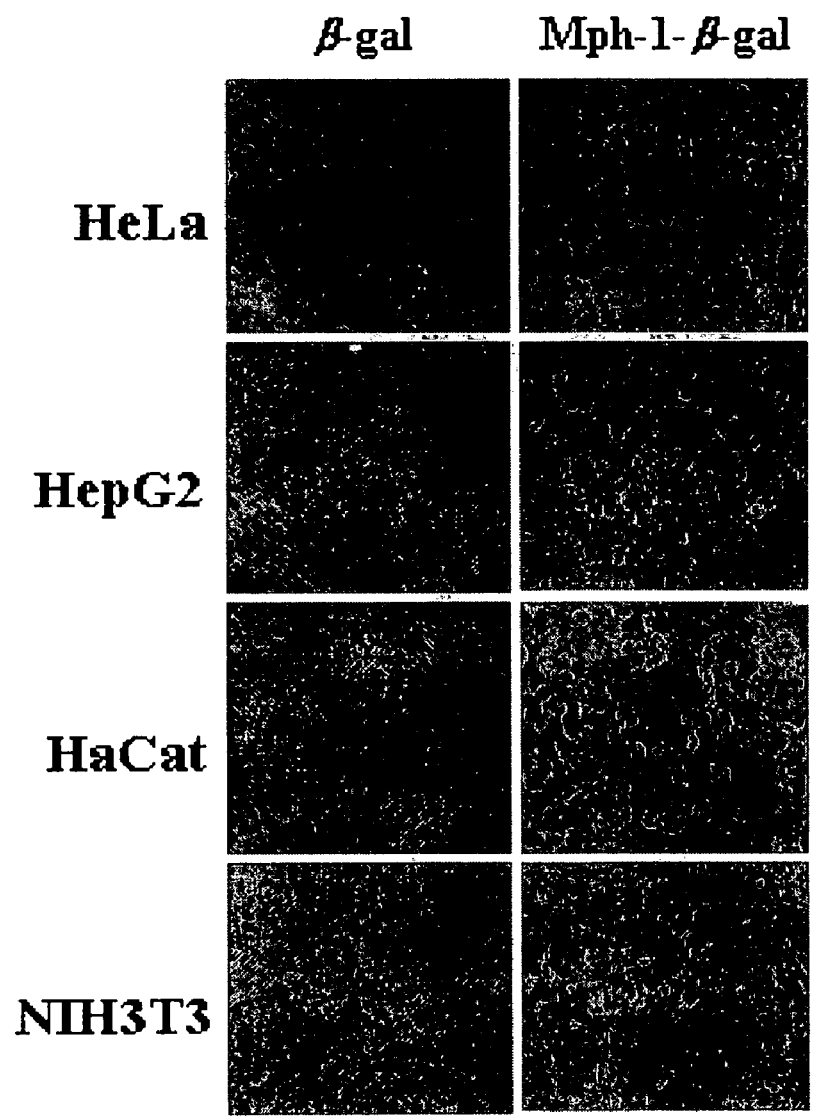

FIG. 1C are photographs of transduction efficiency of Hph-1 in several cell lines, including HeLa, HepG2, HaCat and NIH3T3. After 1 hour incubation with Hph-1-β-gal, cells were fixed and stained with X-gal solution. The images were then captured by fluorescence microscopy.

Figure 1D:
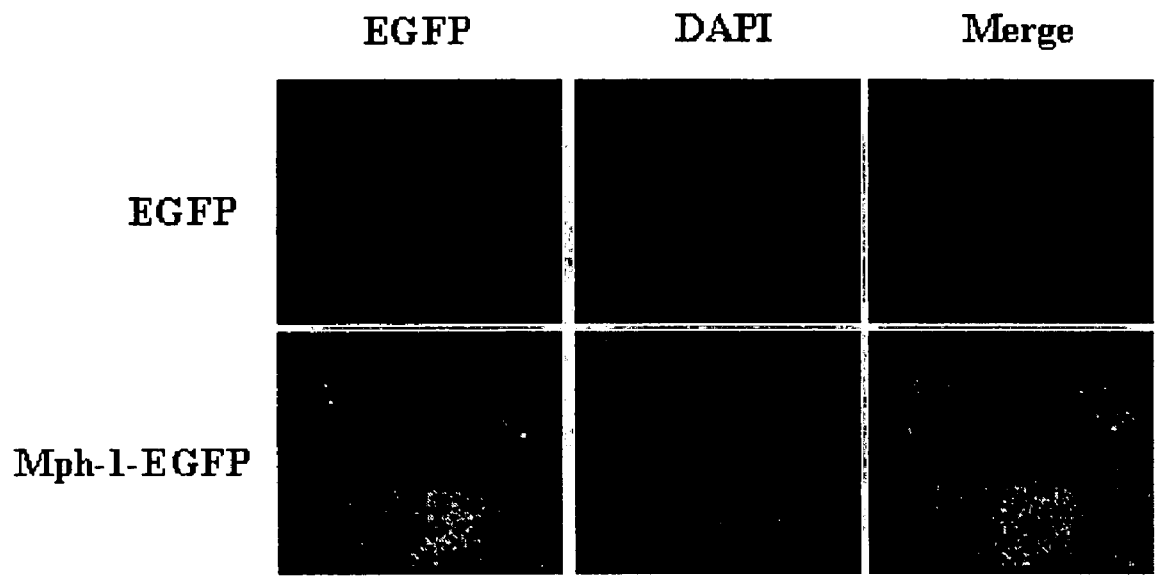

FIG. 1D are photographs of the intracellular localization of Hph-1-FITC, as analyzed by confocal microscopy. After the Hph-1-eGFP and control eGFP proteins were incubated with HeLa cells for 1 hour, the cells were fixed and stained with DAPI.

Figure 1E:
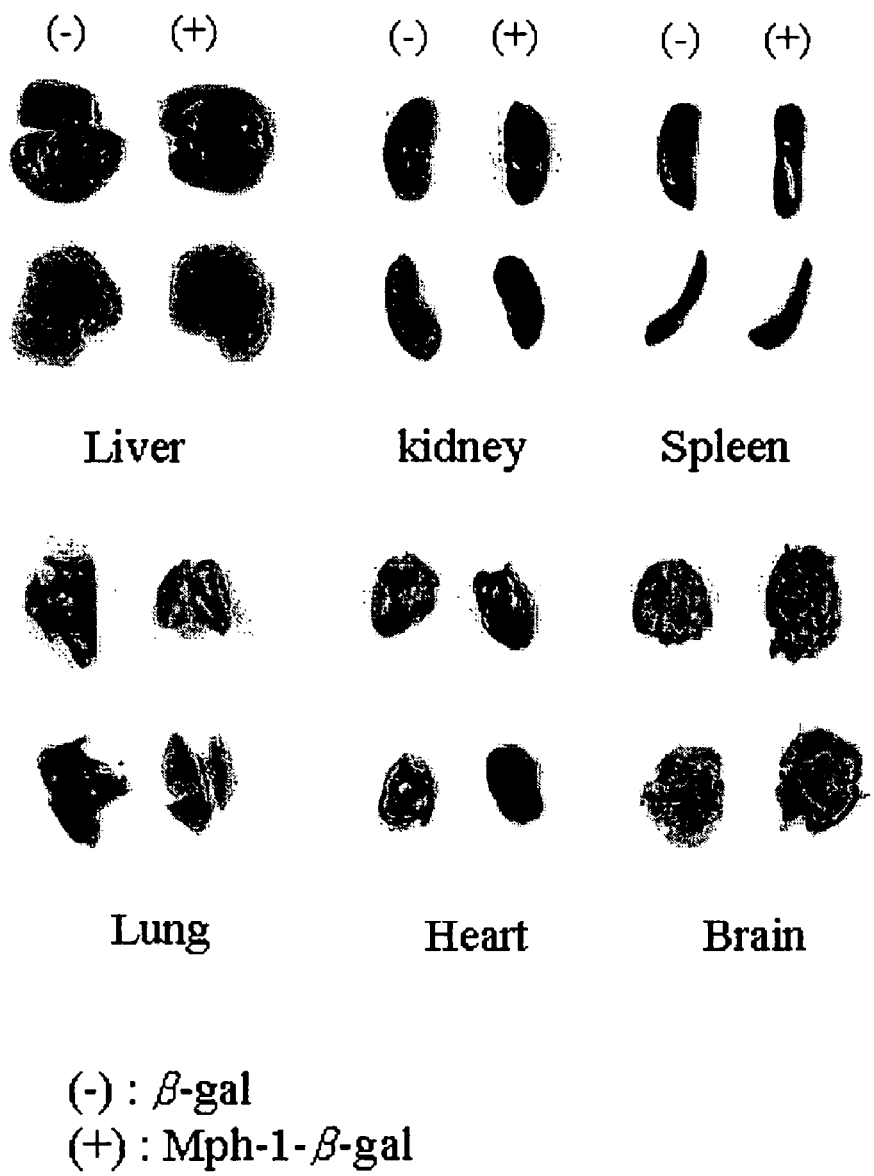

FIG. 1E shows the in vivo transduction efficiency of Hph-1-PTD. Either 5 mg of Hph-1-β-gal or control β-gal was i.p.

injected into mice. The liver, kidney, spleen, lung, heart and brain were excised and fixed, and full organs (top row), thin sections (bottom row) of each were analyzed for the β-gal activity with addition of X-gal solution.

Figure 2A:
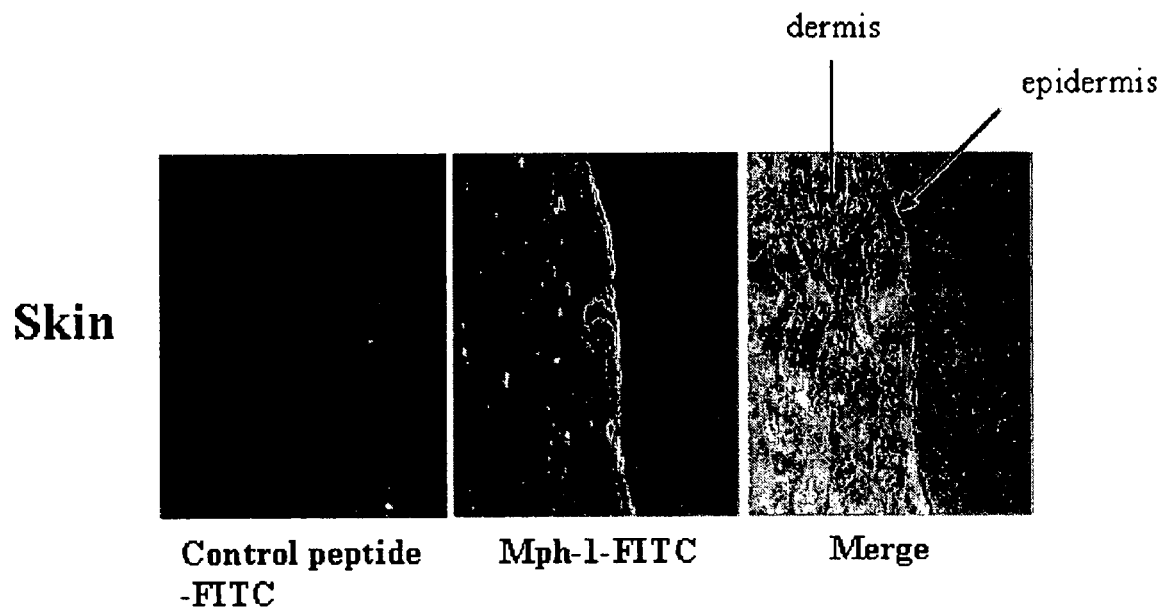

FIG. 2A shows transduction of Hph-1-PTD into the epidermis as well as dermis through the skin. A mixture of Hph-1-FITC and ointment was applied to the stripped skin of hairless mice for 2 hours. The skin sample was analyzed for the presence of fluorescence by confocal microscopy.

Figure 2B:
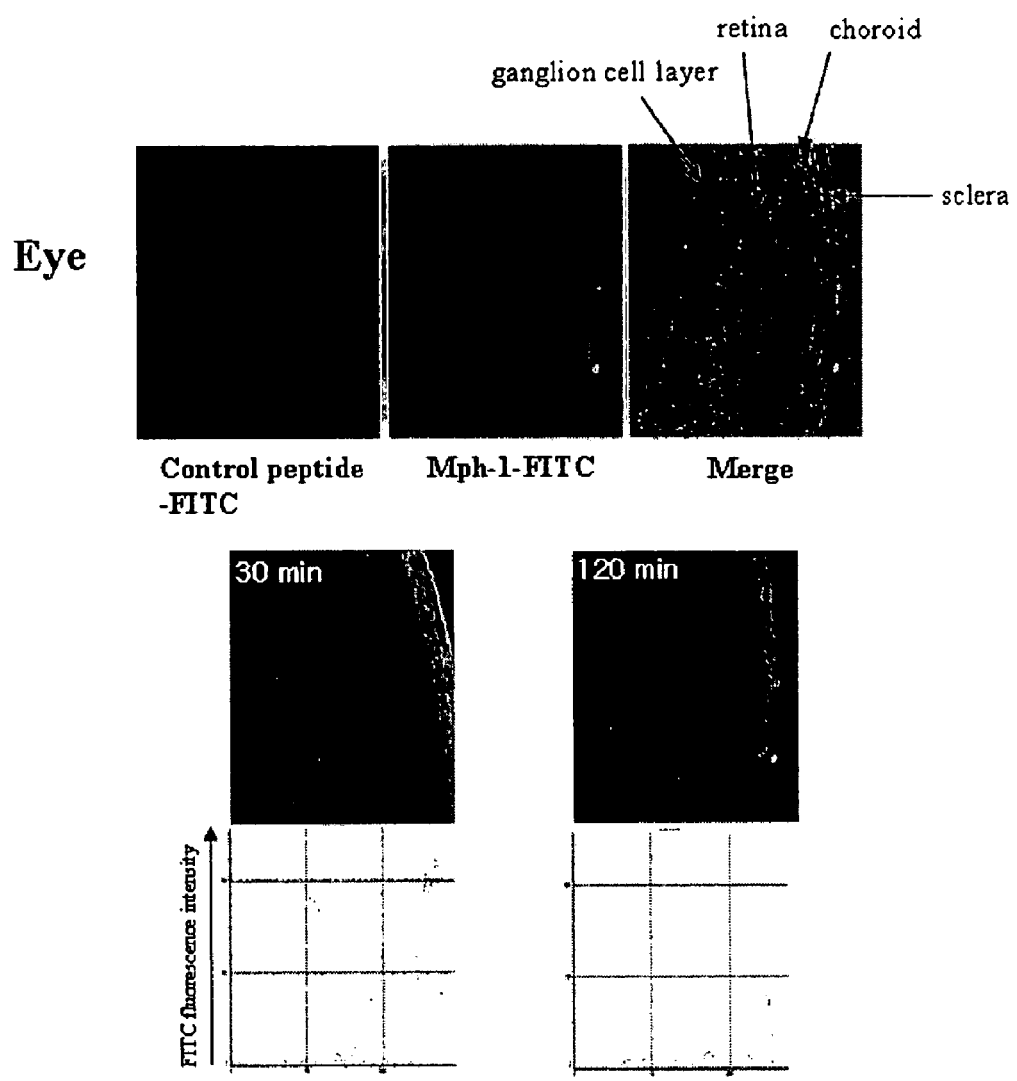

FIG. 2B shows delivery of Hph-1-PTD-FITC into retina and ganglion cell layer through sclera of the eye. Hph-1-FITC solution was dropped on the eye for 30 or 120 min. FITC fluorescence was examined in the frozen section of the eye by confocal microscopy.

Figure 2C:
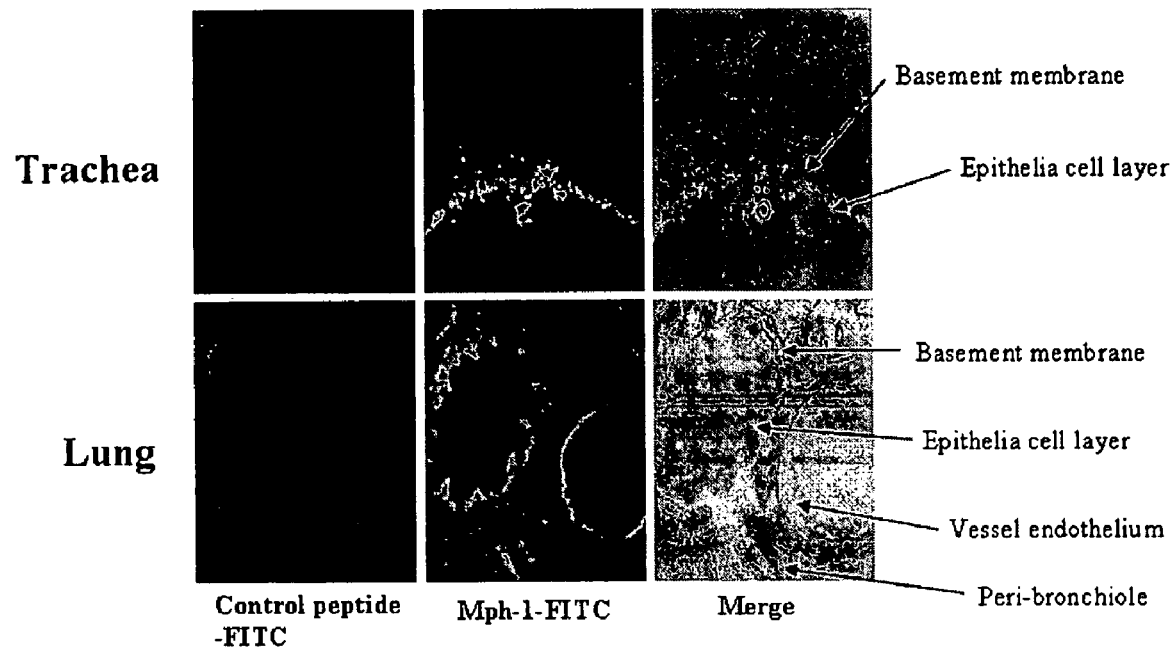

FIG. 2C shows transduction of Hph-1-PTD-FITC through the nasal route. FITC conjugated Hph-1-PTD solution was locally delivered into trachea and lung by intra-tracheal instillation. FITC fluorescence was examined in the bronchi and endothelial area of vessels in the lung and in the basement membrane of the bronchus.

Figure 3A:
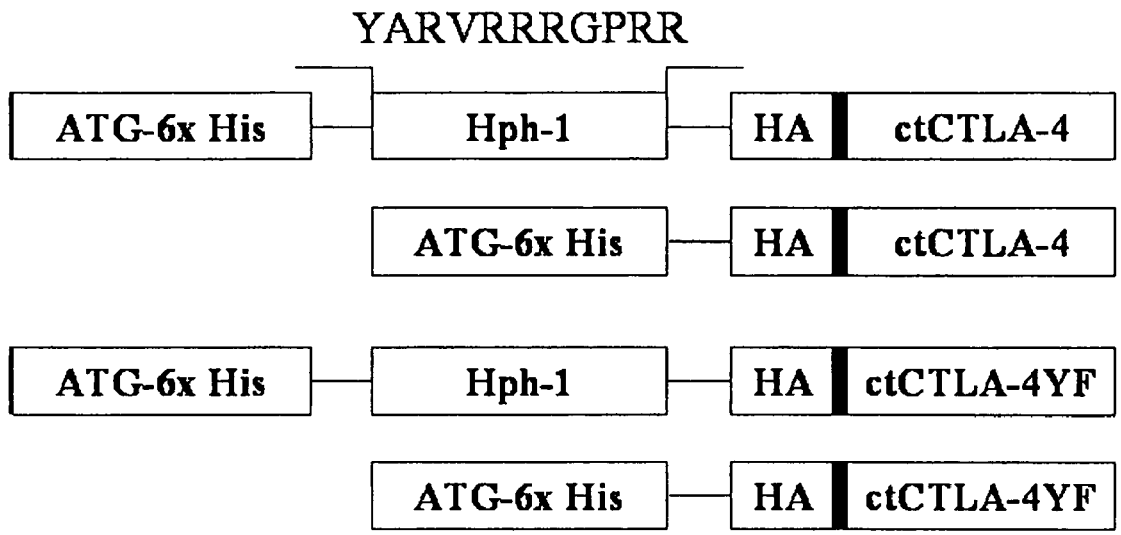

FIG. 3A is a schematic of the Hph-1-ctCTLA-4 (SEQ ID NO: 11) and the Hph-1-ctCTLA-4YF (SEQ ID NO: 19) mutant constructs.

Figure 3B:
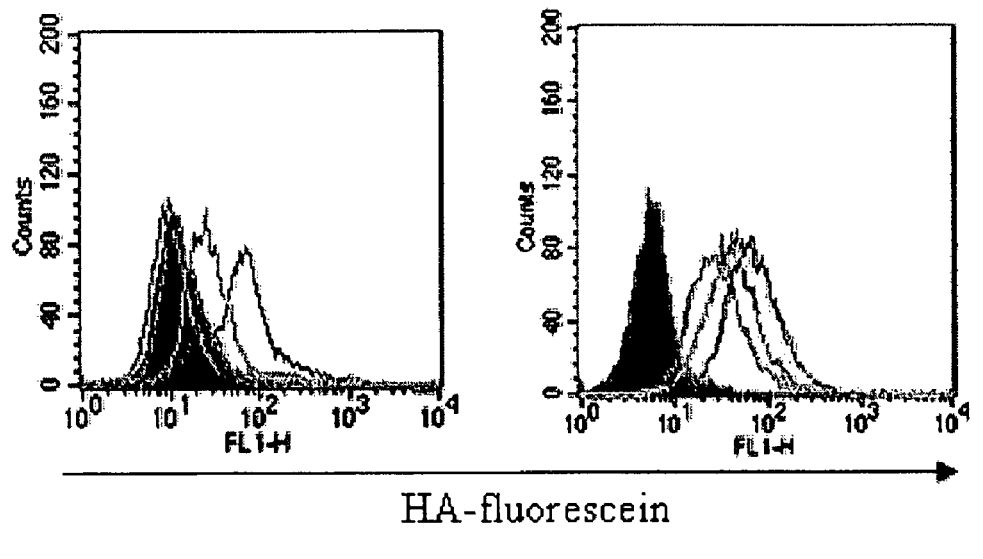
Figure 3C:
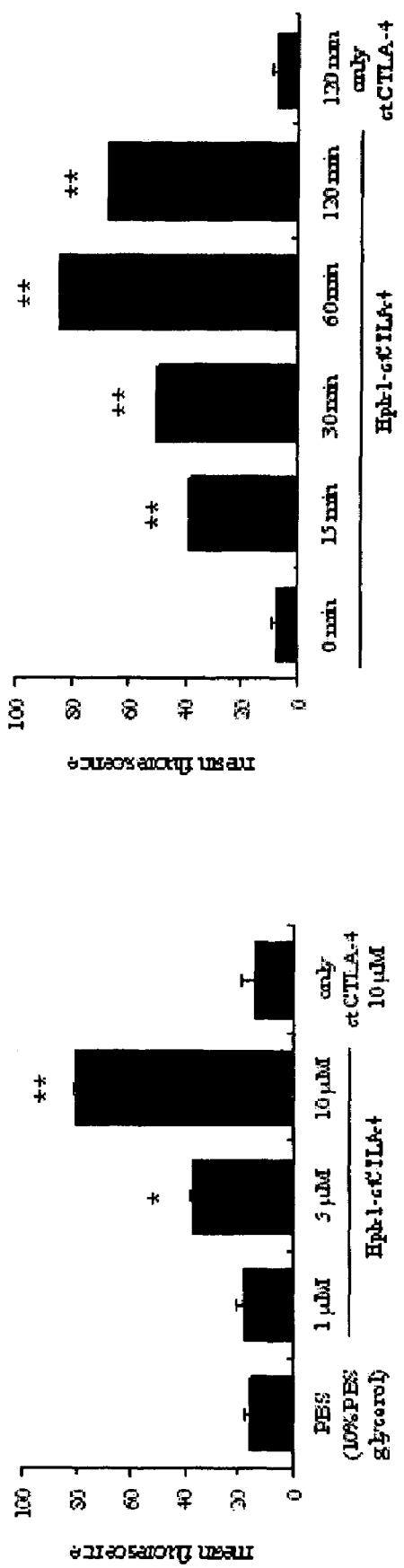

FIGS. 3B-C show results of transduction efficiency and kinetics of Hph-1-ctCTLA-4 in Jurkat T cells (which are known not to express CTLA-4 on the surface), which were analyzed by intracellular staining using anti-HA-fluorescein mAb.

Figure 3D:
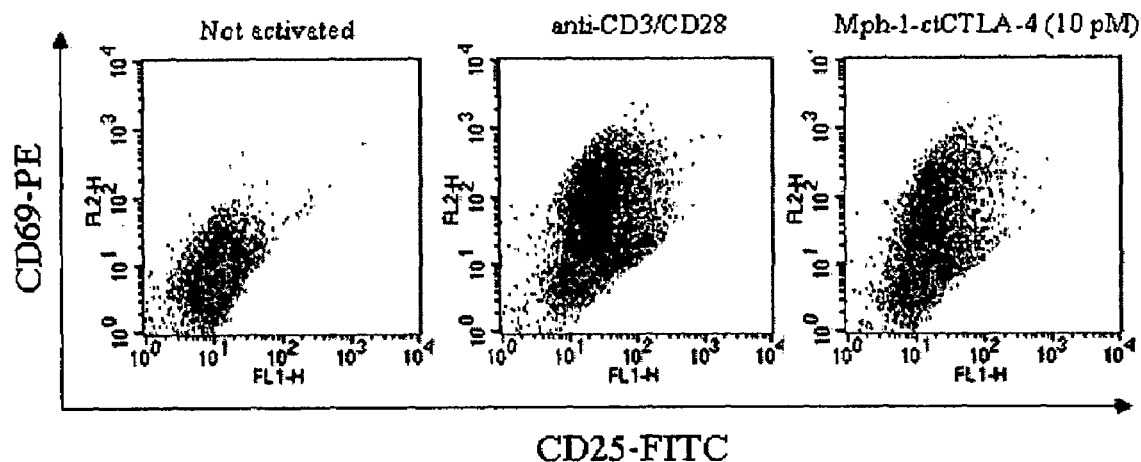
Figure 3E:
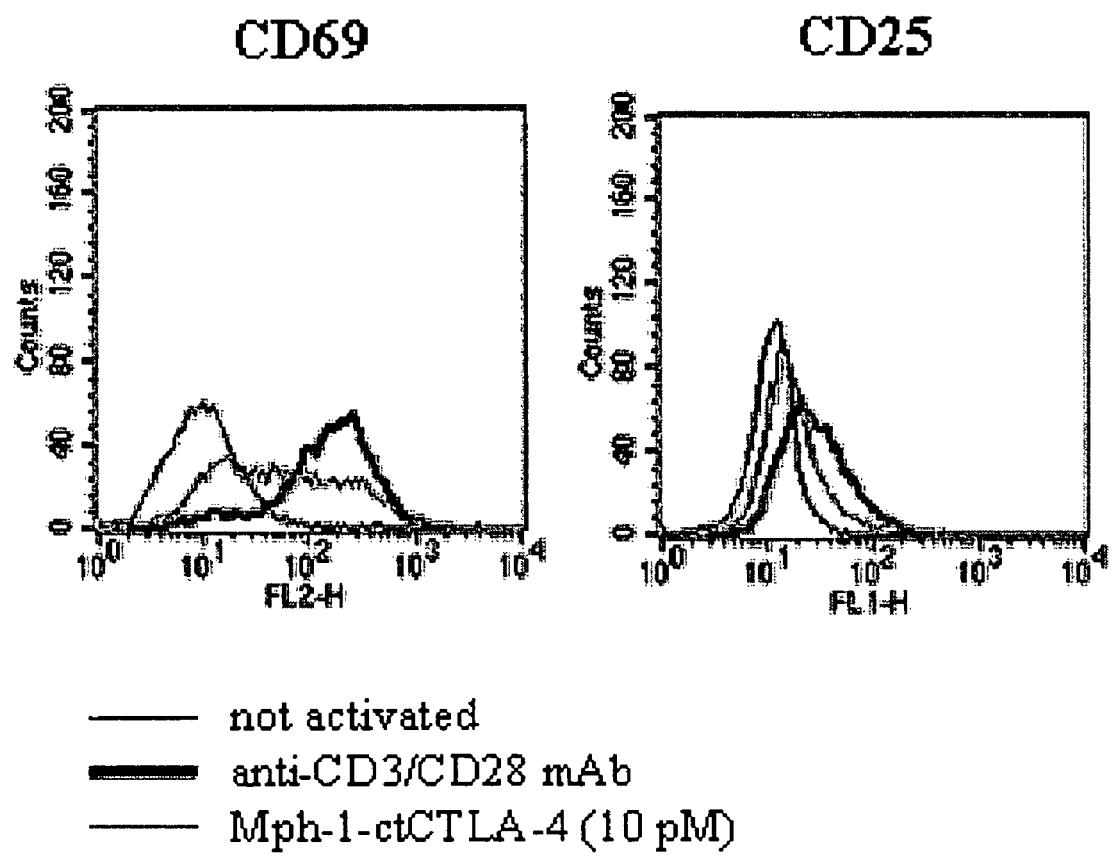

FIGS. 3D-E show that Hph-1-ct-CTLA-4 inhibits induction of CD69 and CD25 expression on the surface of activated T cells.

Figure 3F:
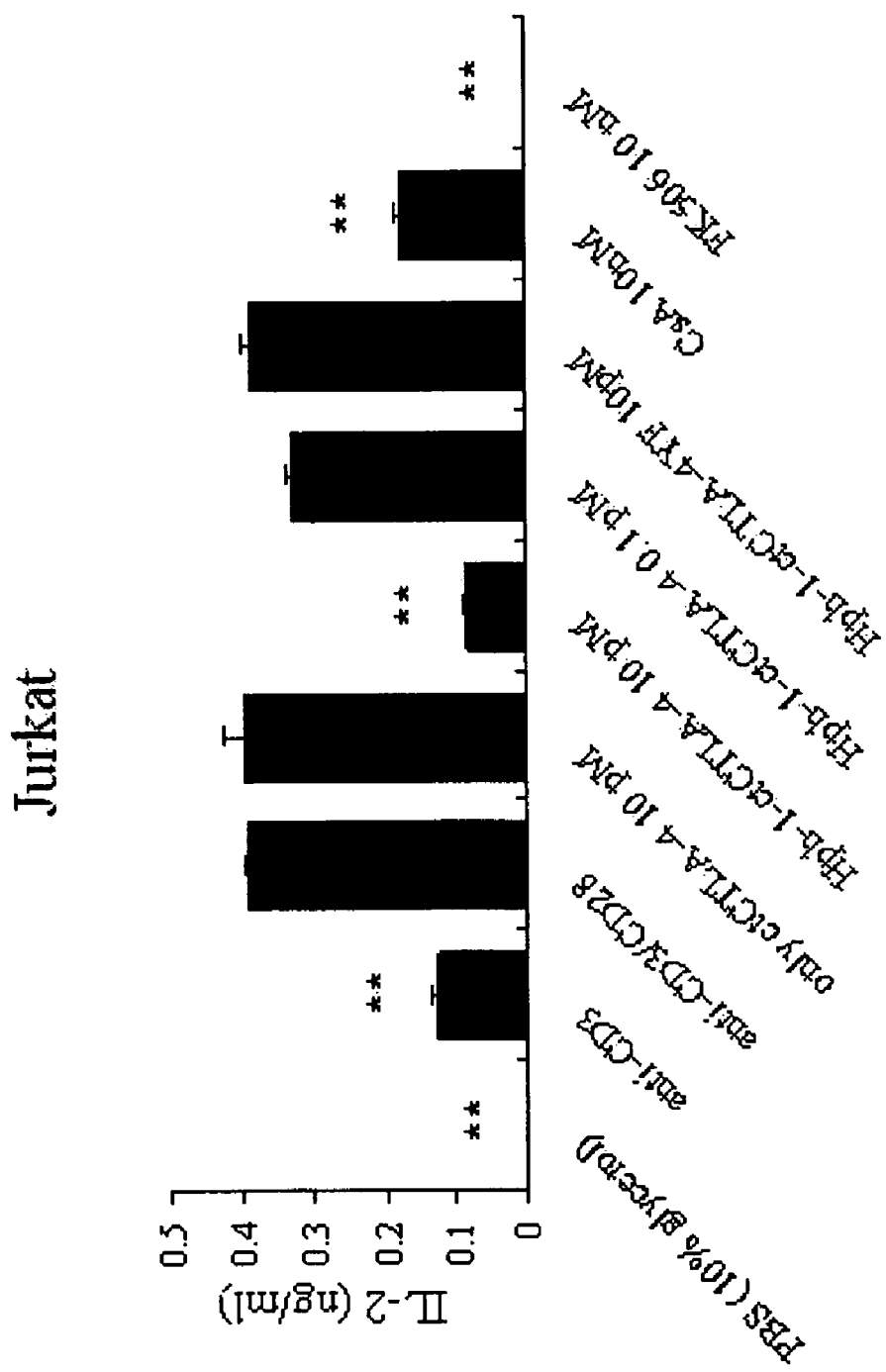
Figure 3G:
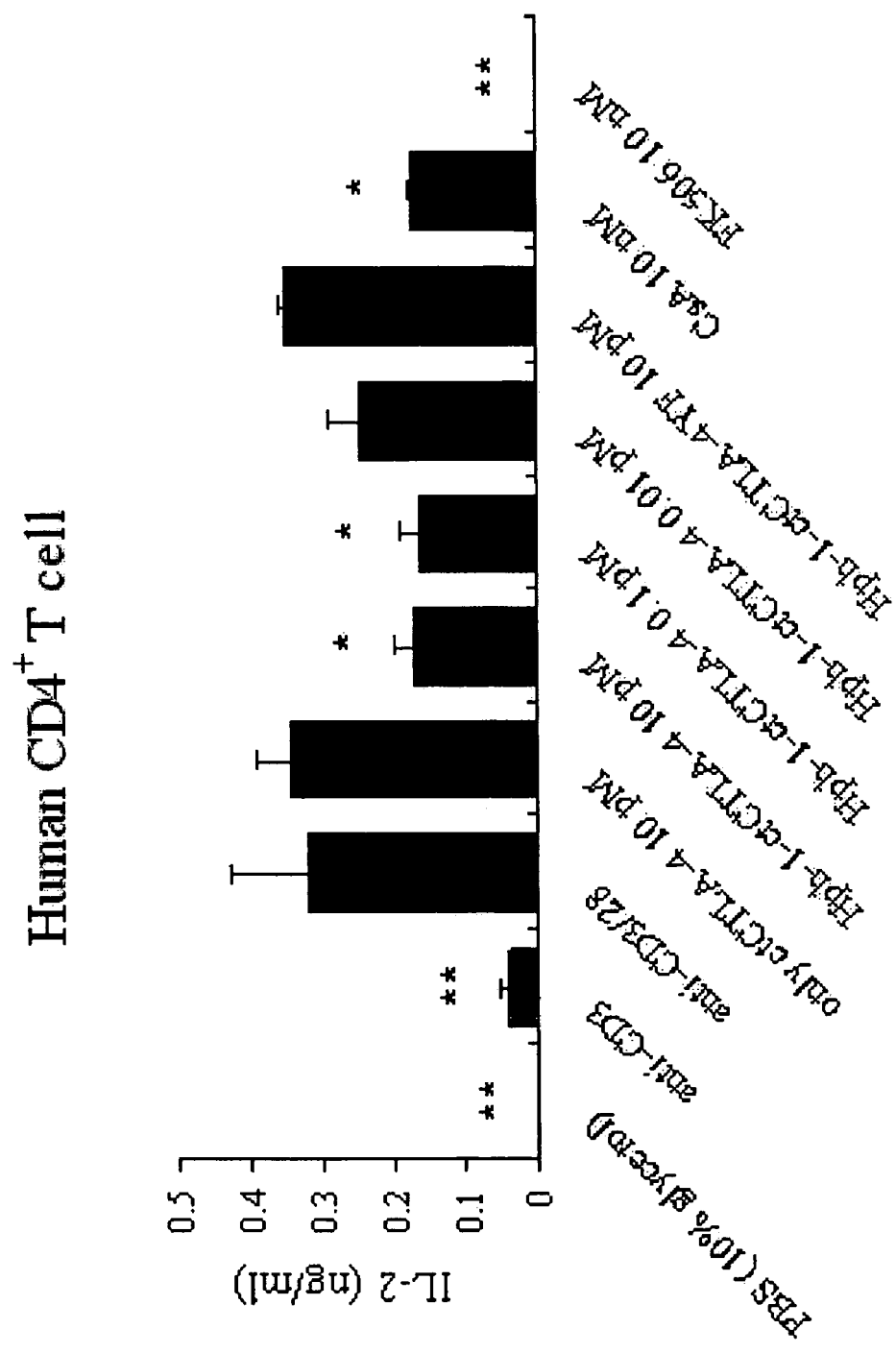

FIGS. 3F-G show inhibition of IL-2 secretion by Hph-1-ctCTLA-4 in activated Jurkat T cells and primary human $CD4^+$ T cells.

Figure 4A:
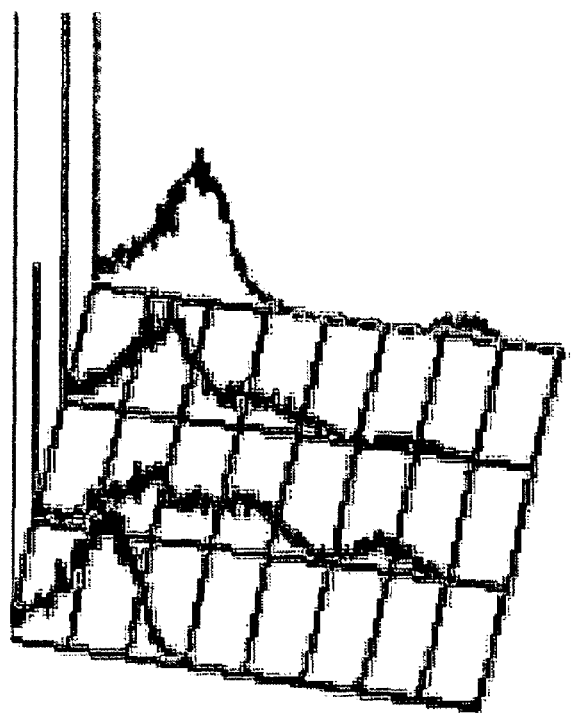
Figure 4B:
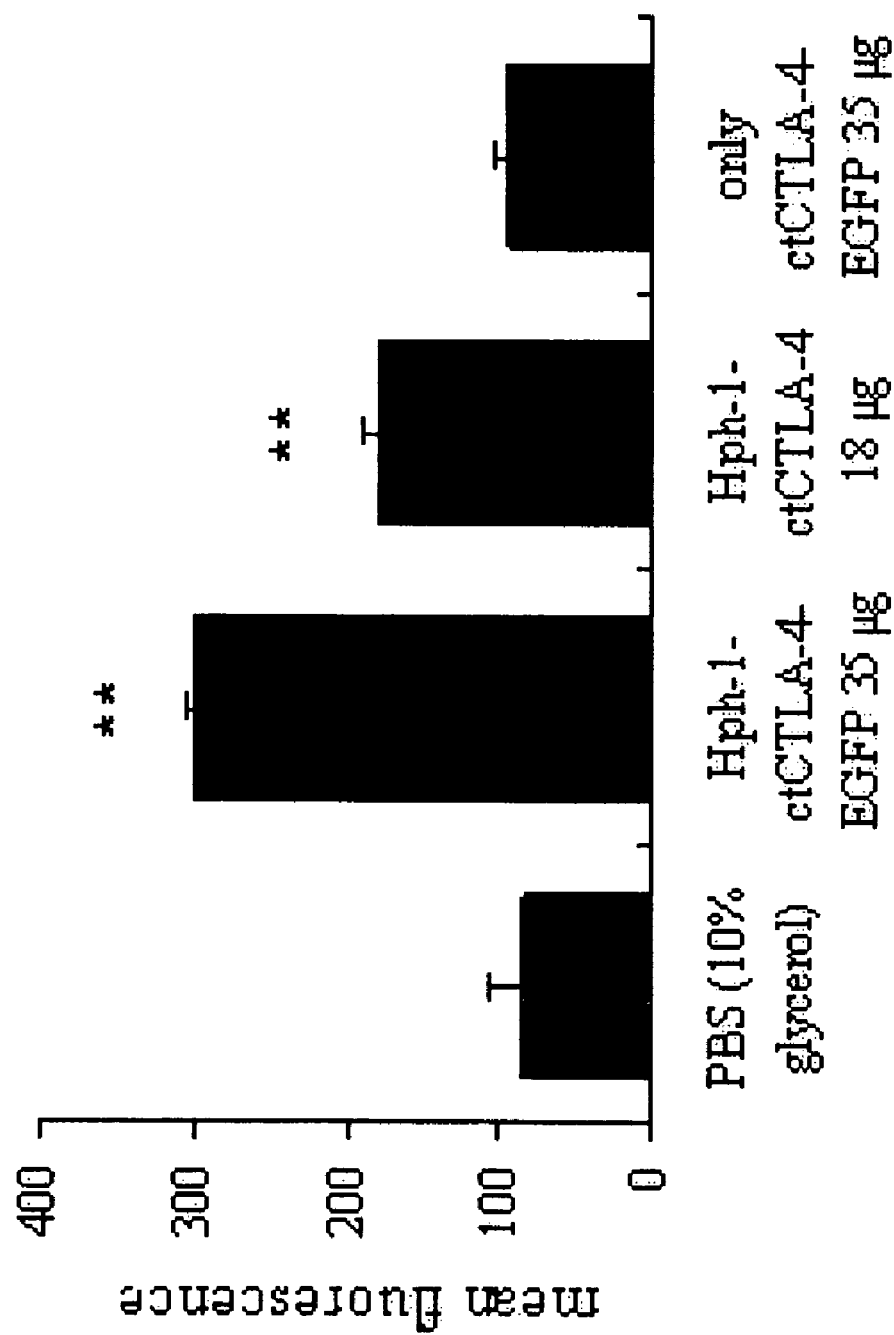
Figure 4C:
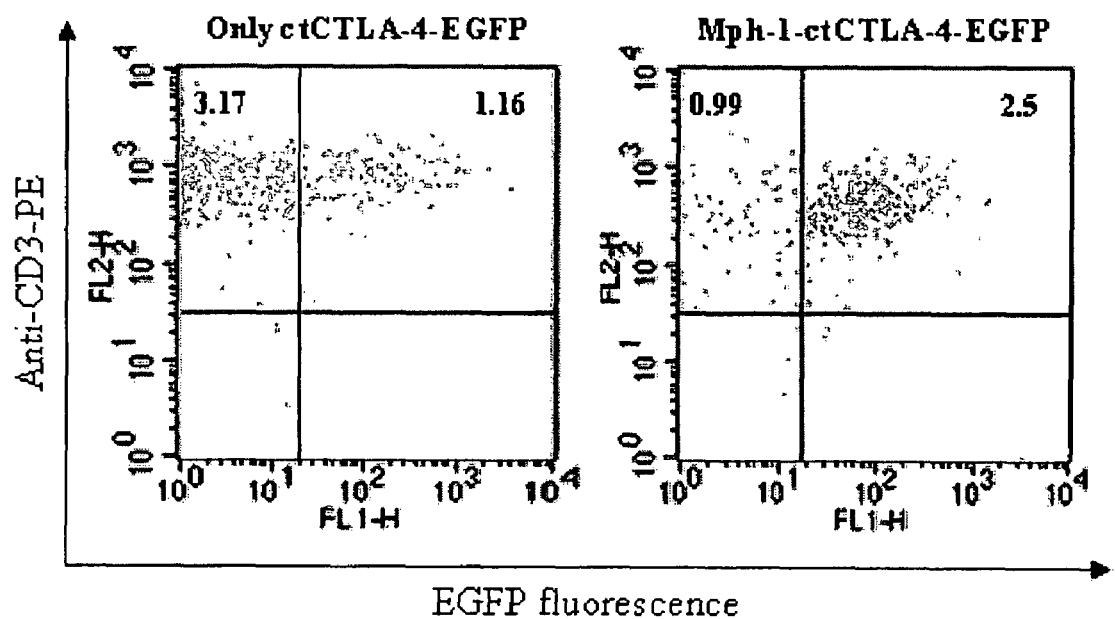

FIGS. 4A-C show transduction of Hph-1-ctCTLA-4-eGFP into bronchoalveolar cells after intra-tracheal instillation in mice. After Hph-1-ctCTLA-4-eGFP or ctCTLA-4-eGFP were administered via the nasal route, the levels of eGFP in the total bronchoalveolar lavage (BAL) cells or the $CD3^+$ T cells in the BAL fluid were analyzed by FACS.

Figure 4D:
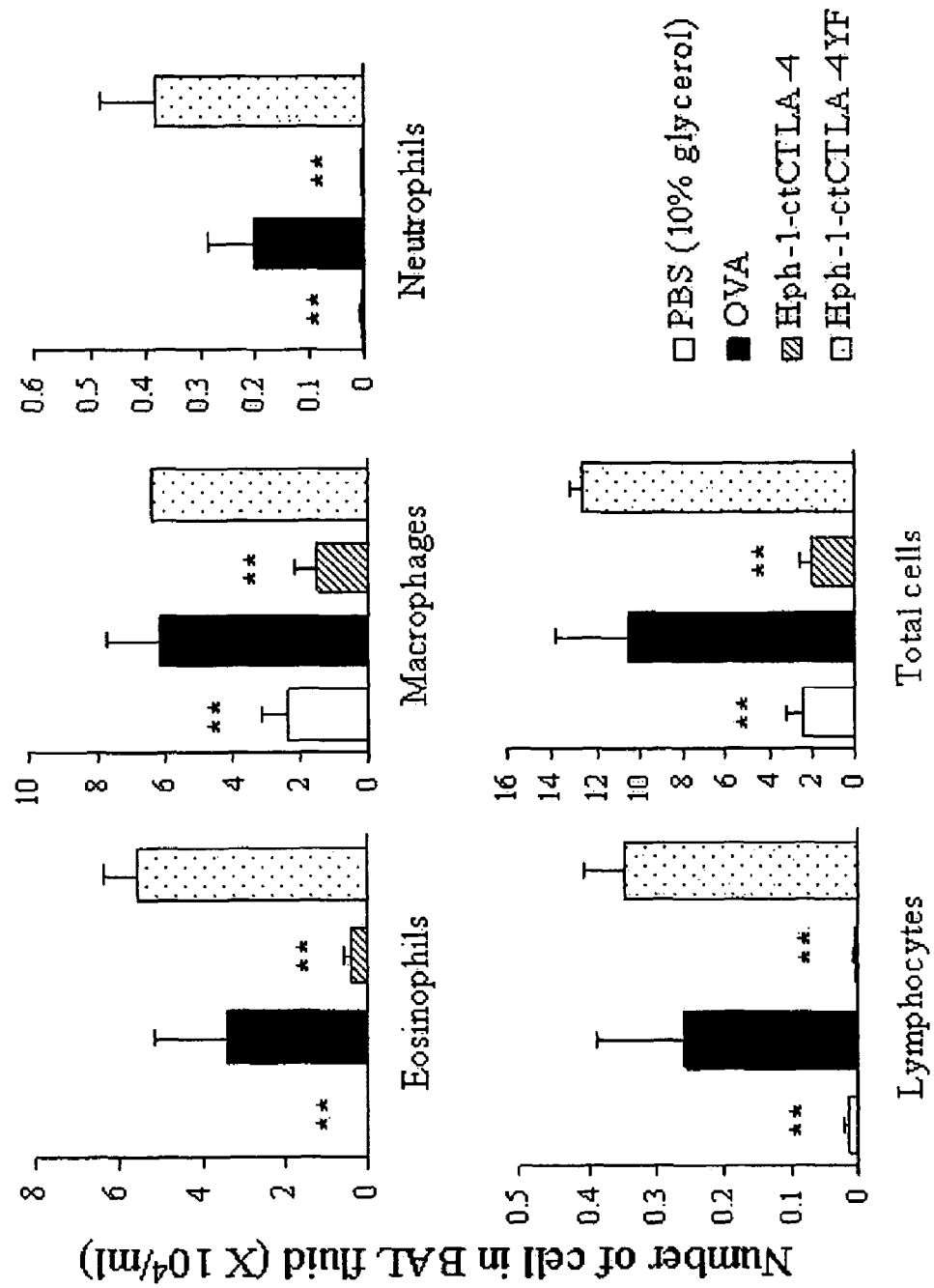

FIG. 4D shows the number of diverse inflammatory cells in BAL fluid (after OVA challenge) observed after intra-nasal pretreatment with Hph-1-ctCTLA-4 or the Hph-1-ctCTLA-4YF mutant.

Figure 4E:
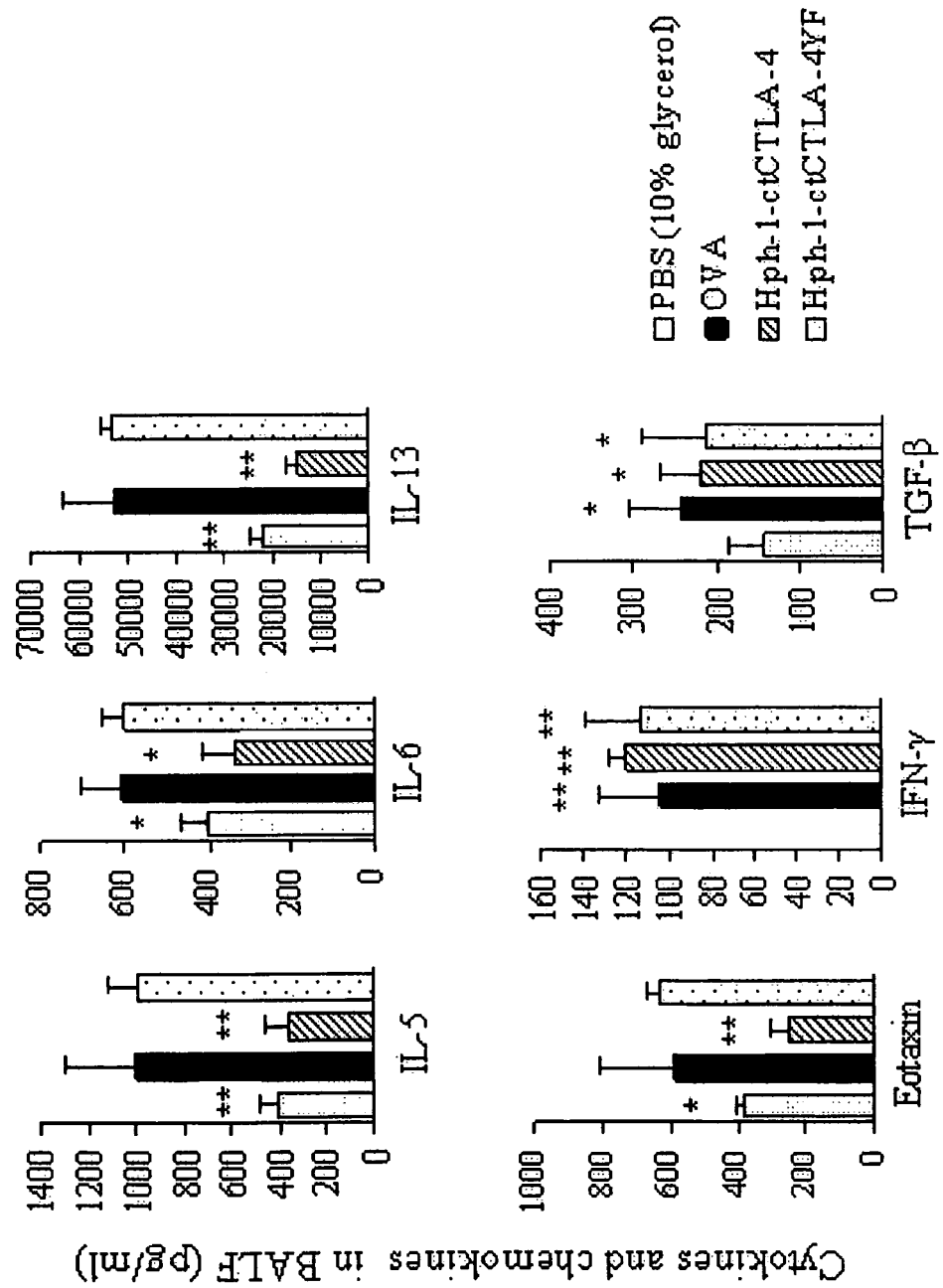

FIG. 4E shows the level of secretion of OVA-induced inflammatory cytokines and chemokines into BAL fluid, analyzed by ELISA following administration of Hph-1-ctCTLA-4 or Hph-1-ctCTLA-4YF mutant through nasal airway.

Figure 4F:
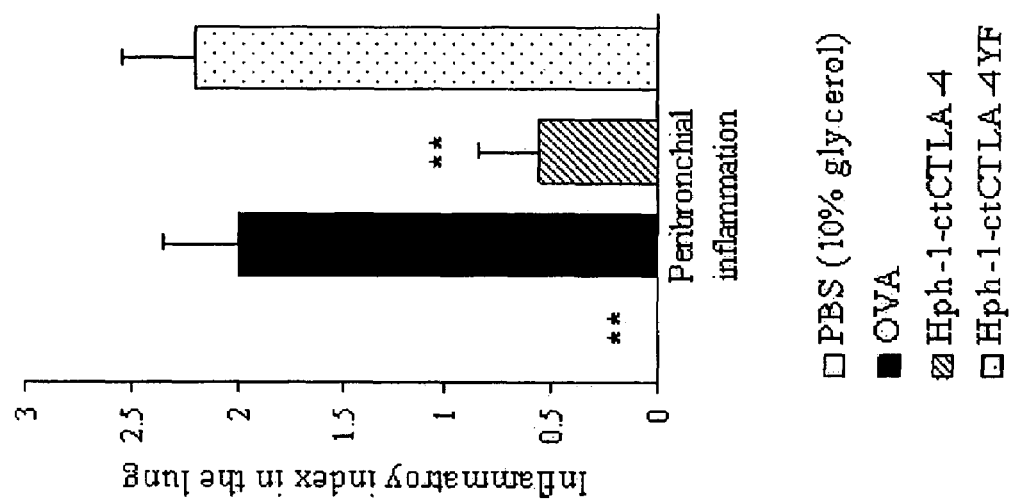

FIG. 4F shows the semi-quantitative analysis of the severity of peribronchial inflammation in OVA-challenged mice pretreated with Hph-1-ctCTLA-4.

Figure 4G:
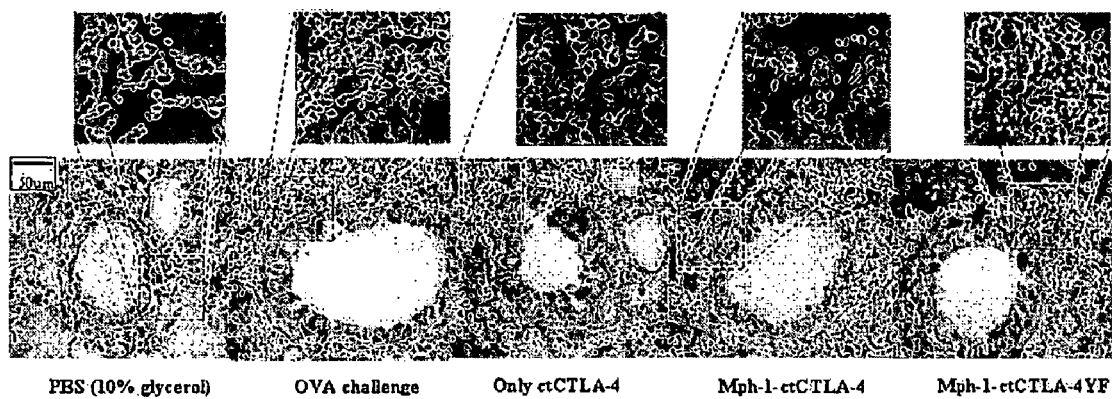

FIG. 4G shows the histological examination of lung tissues after OVA-challenge in control mice and mice treated with Hph-1-ctCTLA-4.

Figure 5A:
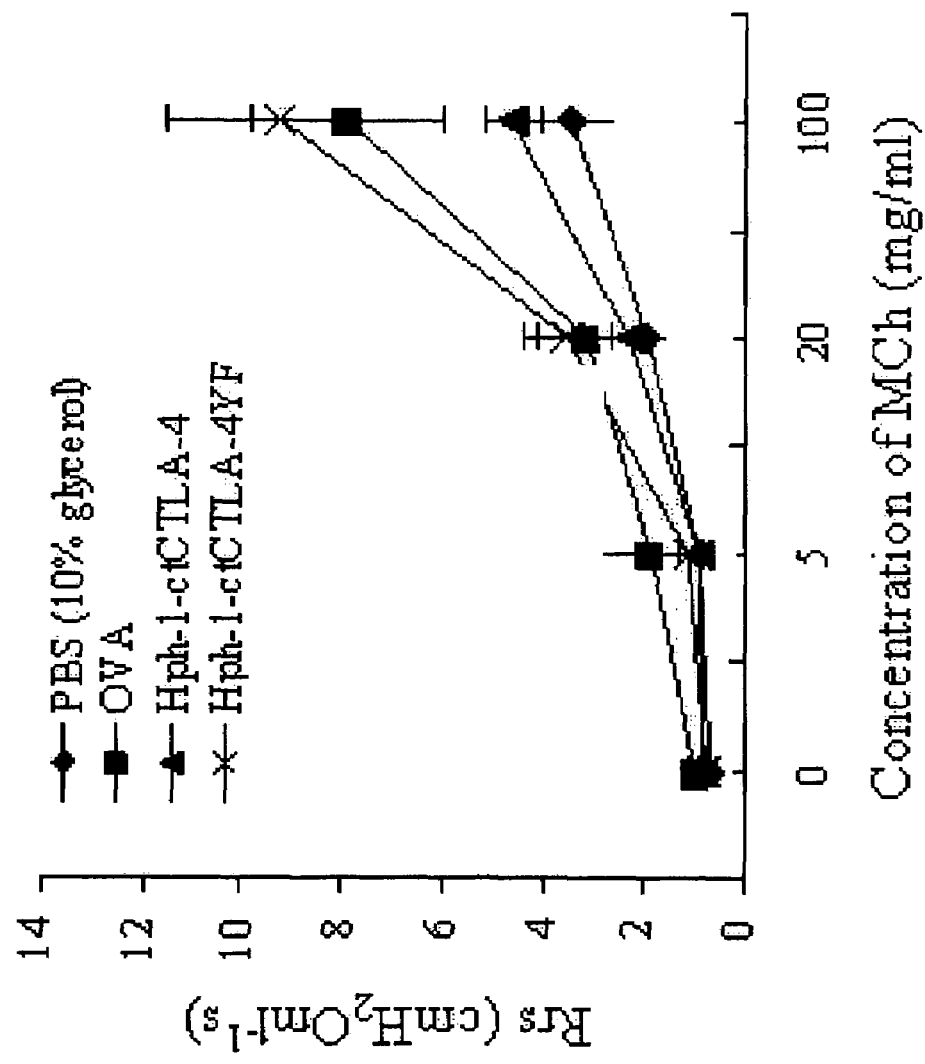
Figure 5B:
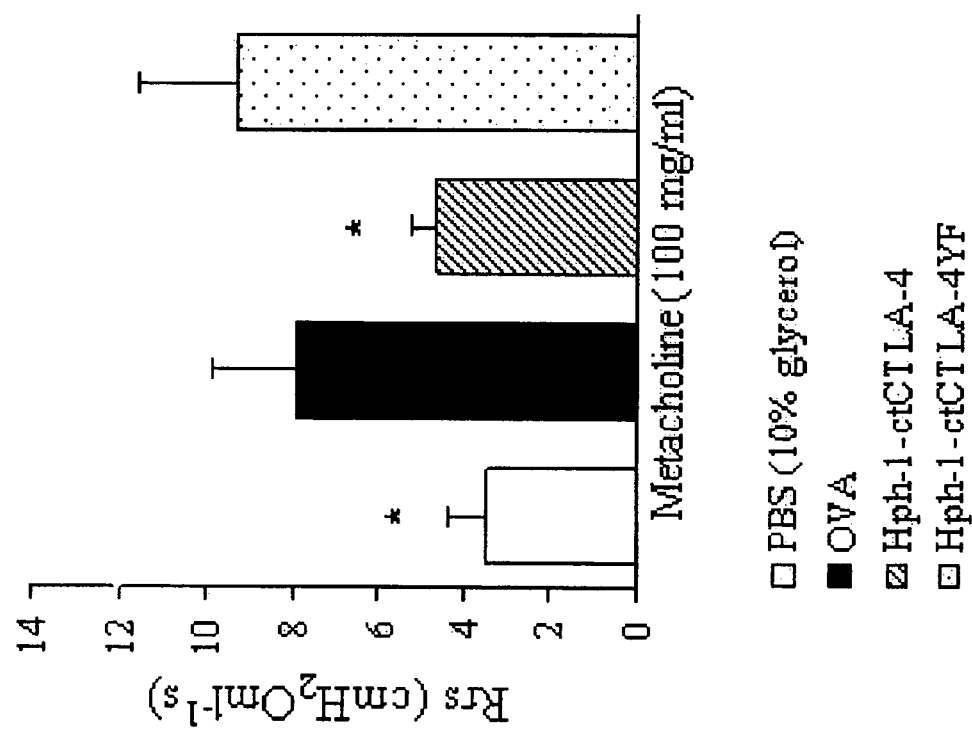

FIGS. 5A-B show inhibitory effects of Hph-1-ctCTLA-4 on antigen-induced airway hyper-responsiveness to methacholine (MCh).

Figure 6:
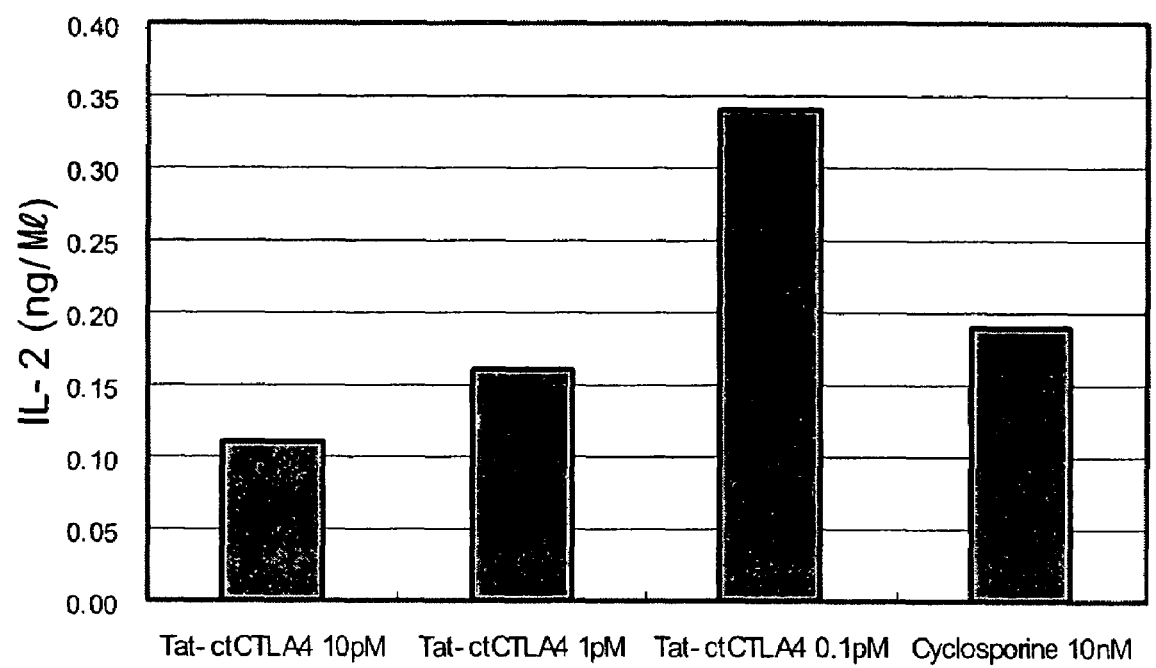

FIG. 6 shows the result of inhibiting IL-2 secretion by Tat-ctCTLA-4 treatment.

Figure 7:
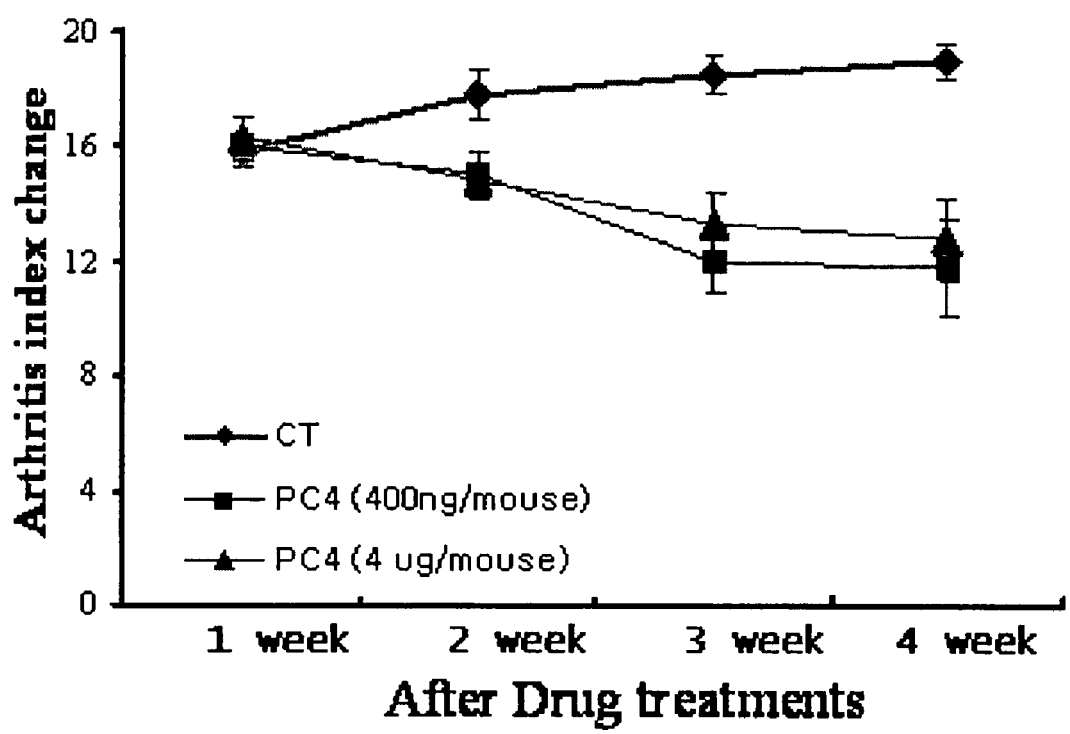
Figure 8:
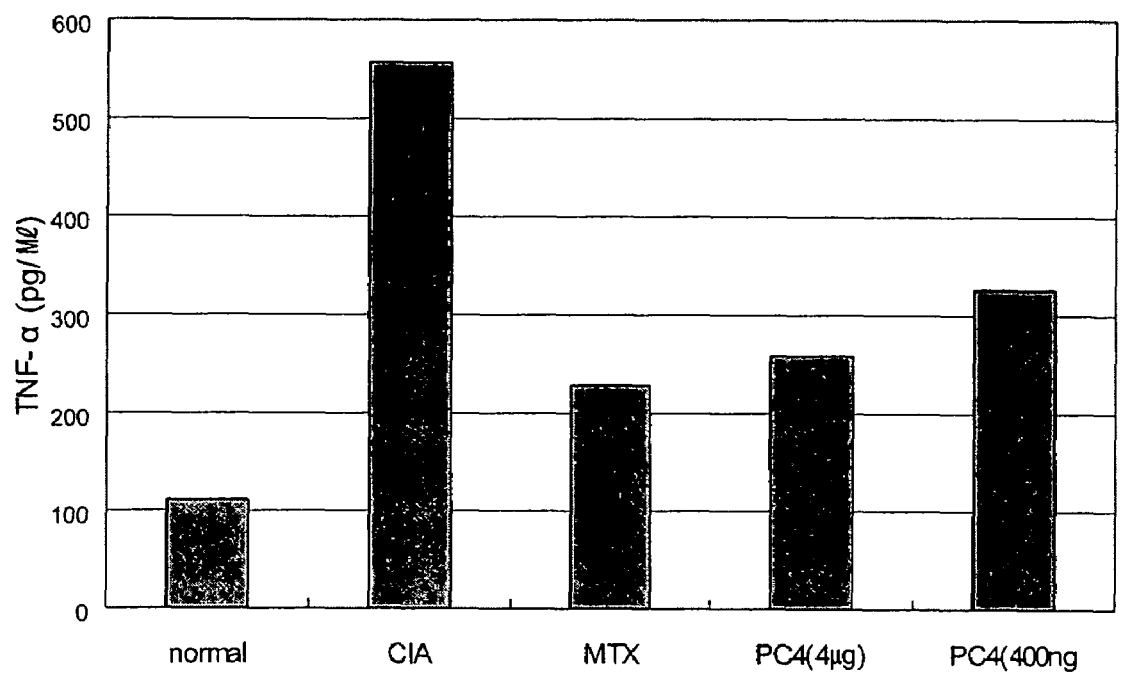
Figure 9:
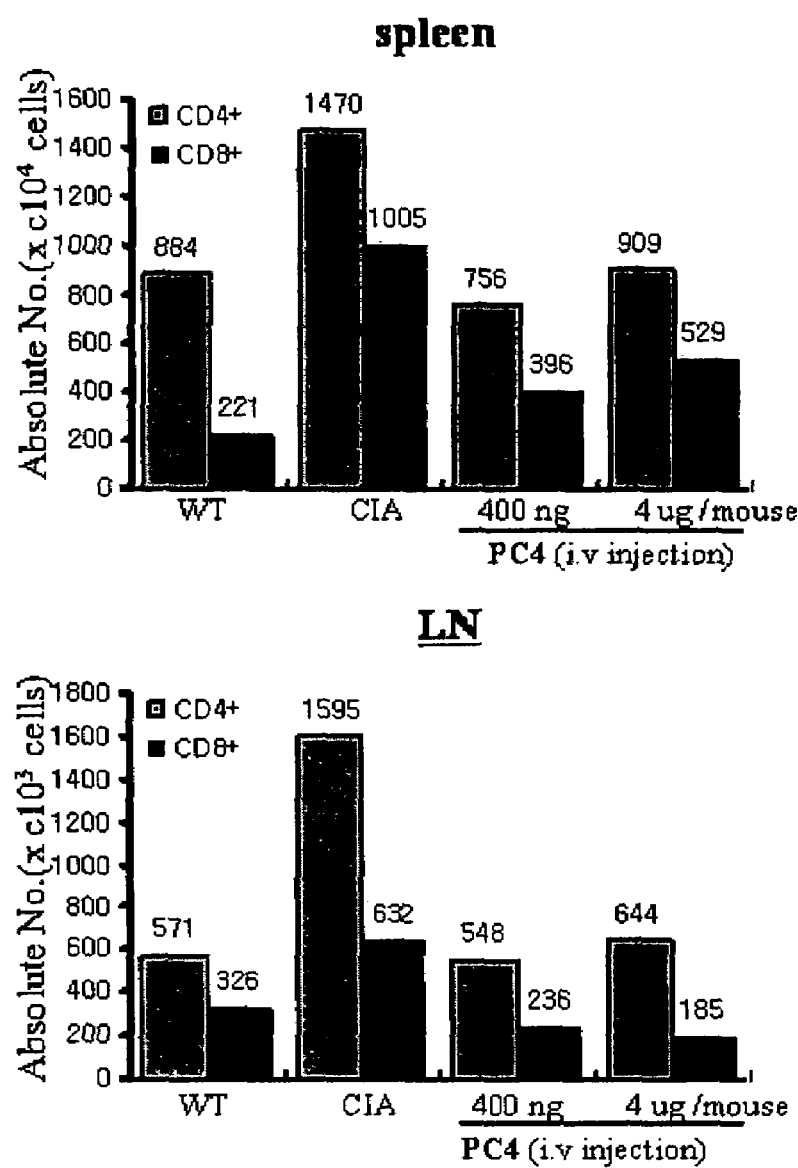

FIGS. 7-9 demonstrate the inhibitory effects of Mph-1-ctCTLA-4 on rheumatoid arthritis animal models induced by intraperitoneal injection of collagen type II.

Figure 10:
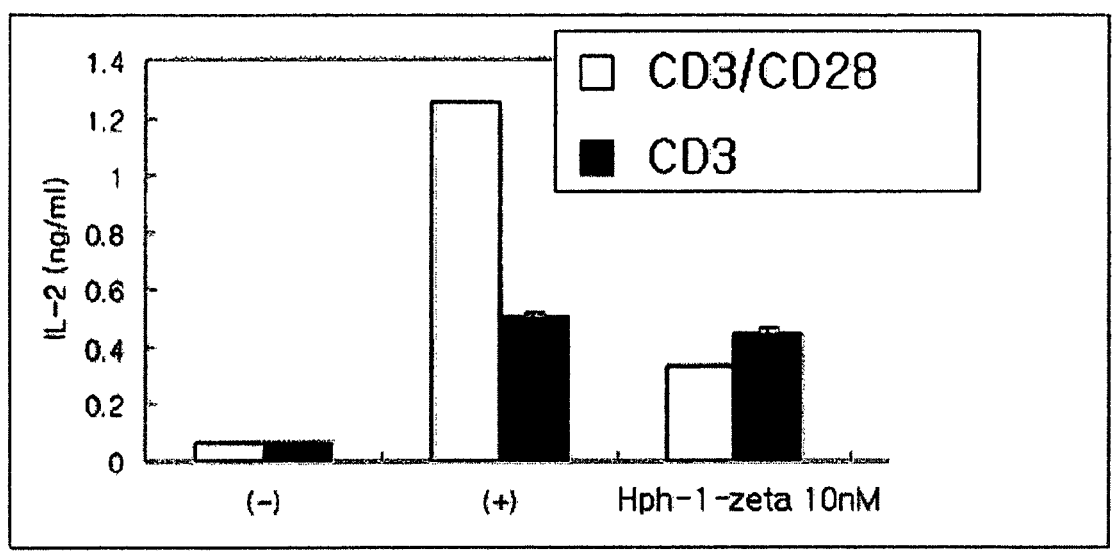

FIG. 10 shows the result of inhibiting IL-2 secretion by Hph-1-ζ-chain treatment.

Figure 11:
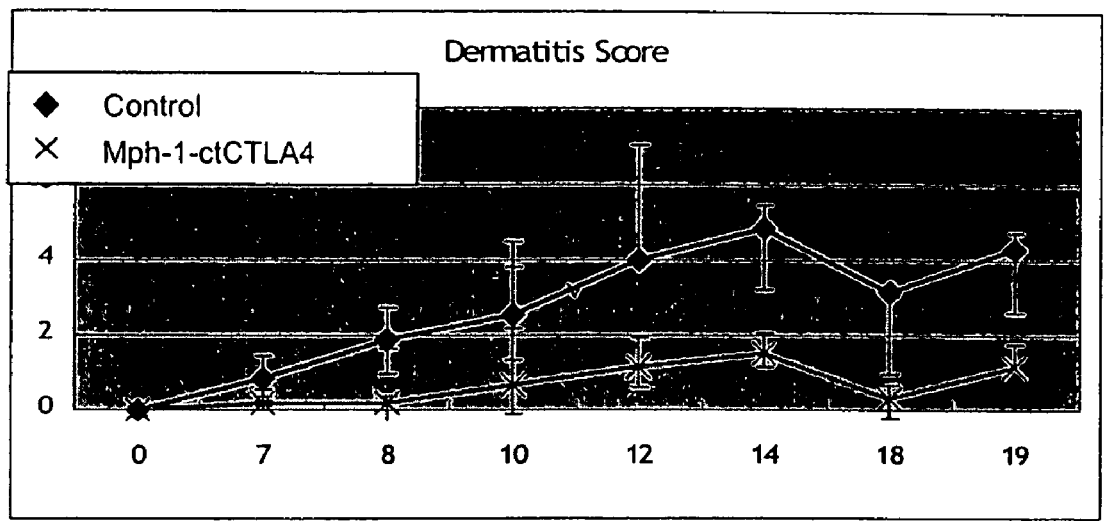

FIG. 11 shows the suppression of inflammation in atopic rats treated with Mph-1-ctCTLA4 compared to control rats as measured by the dermatitis score.

Figure 12:
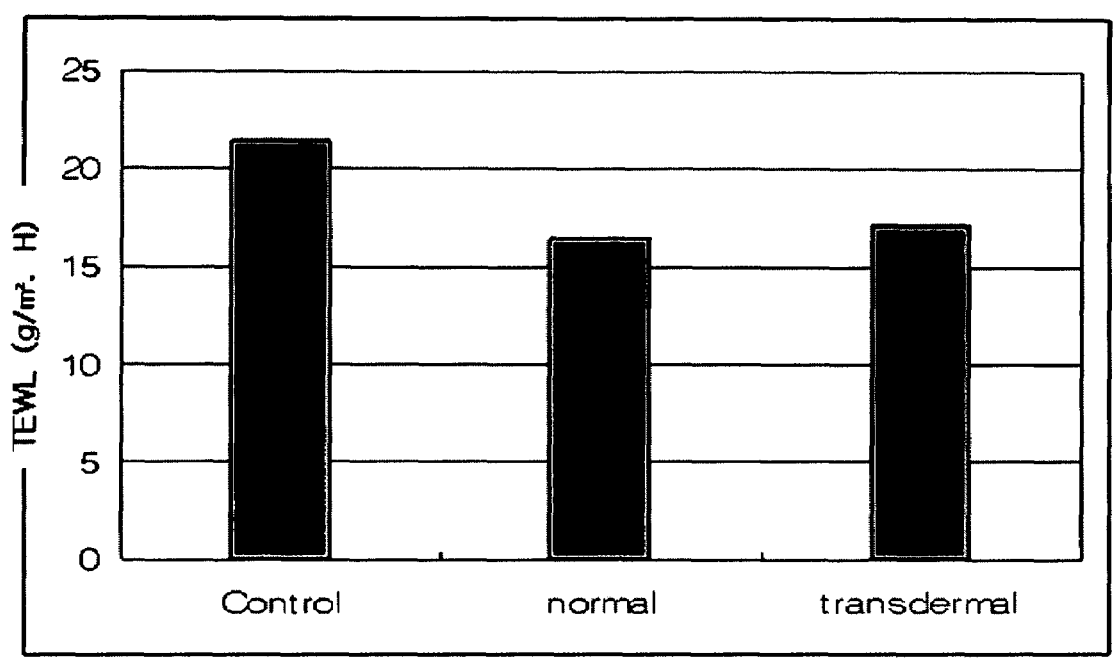

FIG. 12 shows the suppression of inflammation in atopic rats treated with Mph-1-ctCTLA4 compared to control rats as measured by the amount of Transepidermal water loss (TEWL) in $g/m^2 \cdot H$.

DETAILED DESCRIPTION OF THE INVENTION

The present invention provides methods for delivering a biomolecule transduction complex (BTC) comprising a protein transduction domain (PTD) and a molecule of interest, such as a polypeptide. The PTD effectively allows delivery or uptake of a polypeptide of interest in vivo and in vitro into cells by systemic or local administration. Administration routes include routes that are intramuscular, intraperitoneal, intravenous, oral, nasal, subcutaneous, intradermal, mucosal, and inhalation. Our invention enables administration of the resultant fusion polypeptides via local administration routes, thereby minimizing the systemic toxicity.

One embodiment involves the use of Hph-1-PTD, the PTD from the human transcription factor HPH-1 (YARVRRRG-PRR) (SEQ ID NO:1). Other embodiments include, but are not limited to, the PTDs of mouse transcription factor Mph-1 (YARVRRRGPRR) (SEQ ID NO:2), Sim-2 (AKAAR-QAAR) (SEQ ID NO:3), HIV-1 viral protein Tat (YGRKKRRQRRR) (SEQ ID NO:4), Antennapedia protein (Antp) of *Drosophila* (RQIKIWFQNRRMKWKK) (SEQ ID NO:5), HSV-1 structural protein Vp22 (DAATATRGR-SAASRPTERPRAPARSASRPRRPVE) (SEQ ID NO:6), regulator of G protein signaling R7 (RRRRRRR) (SEQ ID NO:7), MTS (AAVALLPAVLLALLAPAAADQNQLMP) (SEQ ID NO:8), and short amphipathic peptide carriers Pep-1 (KETWWETWWTEWSQPKKKRKV) (SEQ ID NO:9) and Pep-2 (KETWFETWFTEWSQPKKKRKV) (SEQ ID NO:10).

The desired polypeptide linked to a PTD can be the cytoplasmic domain of a receptor protein. The invention of using the cytoplasmic domain of a receptor protein as a cargo protein for a PTD overcomes the lack of tissue specificity of the cationic PTDs which limited their in vivo utility. One aspect of our invention enables the development of new therapeutic agents which comprise a PTD fused to a protein of interest, such as ctCTLA-4 (SEQ ID NO:11) and ζ-chain (also referred to as the zeta or z chain) (SEQ ID NO:12). The ζ-chain is the cytoplasmic domain of the T cell receptor, which contains three immunoreceptor tyrosine-based activation motifs (ITAMs). It exists as a homodimer of three pairs of tyrosine residues. The three pairs are referred to as the A1A2 (SEQ ID NO:13), B1B2 (SEQ ID NO:14) and C1C2 (SEQ ID NO:15) domains for the purpose of describing the present invention. The cytoplasmic domain of a receptor protein for the present invention can be the entire ζ-chain, an individual ITAM containing a pair of tyrosine residues (i.e., A1A2, B1B2 or C1C2), or any combination of two of the domains, i.e., A1A2-B1B2, A1A2-C1C2 or B1B2-C1C2.

Another protein of interest that may be linked to a PTD is the cytoplasmic domain of PD-1 (programmed death-1 receptor) (SEQ ID NO:16).

In some embodiments, the desired polypeptide linked to a PTD is a reporter protein, e.g., eGFP (SEQ ID NO:17) or β-Gal (SEQ ID NO:18).

The amino acid sequences of the proteins mentioned above are as follows:

ctCTLA-4 (KMLKKRSPLTTGVYVKMPPTEPECEKQFQPYFIPIN); (SEQ ID NO: 11)

The ζ-chain:
FLRVKFSRSAEPPAYQQGQNQLYNELNLGRREEYDVLDKRRGRDPEMGGKPRR KNPQEGLYNELQKDKMAEAYSEIGMKGERRRGKGHDGLYQGLSTATKDTYDA LHMQALPPR; (SEQ ID NO: 12)

ITAM A (A1A2):
NQLYNELNLGRREEYDVLDKRRGRDPEMGGKPRR; (SEQ ID NO: 13)

ITAM B (B1B2):
KNPQEGLYNELQKDKMAEAYSEIGMKGERRRG; (SEQ ID NO: 14)

ITAM C (C1C2):
KGHDGLYQGLSTATKDTYDALHMQALPPR; (SEQ ID NO: 15)

PD-1:
RAARGTIGARRTGQPLKEDPSAVPVFSVDYGELDFQWREKTPEPPVPCVPEQTEY ATIVFPSGMGTSSPARRGSADGPRSAQPLRPEDGHCSWPL; (SEQ ID NO: 16)

eGFP:
MVSKGEELFTGVVPILVELDGDVNGHKFSVSGEGEGDATYGKLTLKFICTTGKLP VPWPTLVTTLTYGVQCFSRYPDHMKQHDFFKSAMPEGYVQERTIFFKDDGNYKT RAEVKFEGDTLVNRIELKGIDFKEDGNILGHKLEYNYNSHNVYIMADKQKNGIK VNFKIRHNIEDGSVQLADHYQQNTPIGDGPVLLPDNHYLSTQSALSKDPNEKRDH MVLLEFVTAAGITLGMDELYKSGRTQISSSSFEFCSRRYRGPGIHIRI and; (SEQ ID NO: 17)

β-Gal:
MELWKSCIFLFLNFCIQSEGIVRTSYGNWNIPKIGDRNIPSFLIDESKNQFLLDGLPF RYISGSIHYFRIPRDRWDERLGKVRALGFNAIQYYIPWNMHELEEGNHDFSGLLD FAEFSMMAFHKYGLWTILRVGPYICGELENGGLPWWLLNKNVTKQRSSDRVFT REVENWFEILLPRVKPLLRKNGGPVLMLQIENEYGSYDACDQQYLRFLRDLTRSL VGDDVLLFTTDGSAESLLKCGTVEGVFPTVDFGPTDDAKEIENNFKLQRKFAPNG PLVNSEYYPGWLVLWGQKKQNLPSPQTIINGSQTMYSLGASFNYYMIHGGTNFG FWNGAETEAPCITSYDYDAPISESGDVTTKYLEIRKWIKGLTDWPTPPLDVPGNSP KGRFGKIKMRLVHSVEKLKTLTSLGDPGDCVETDKPISFETLKHPLGLVAYQAKI NSCGNLTWSFGDFVHVYLNGKYIDTLTRRYYNLTRNSVIIEGCLENEENRLFMLV ENQGRKTFETINDRKGILSDVFMNGQAIQFWTQCGIKLPLQEDFYFRKAMIRNNY RKNVKSNQKQGVFIGILSVDAPTDTWLDTTGWGKGIAIVNGRNFGRYWPTKGPQ MTLYIPAEFLKIGENSVMMVELEGAEEACTSTSSCIADFIDHPVFDFQ. (SEQ ID NO: 18)

The cytoplasmic domain of a receptor protein can be fused with a PTD using routine methods known to those having ordinary skill in the art. The resultant therapeutic fusion polypeptide can effectively inhibit the induction of activation-induced surface proteins, as well as the production of IL-2, at picomolar concentration.

Definitions

The terms "cytoplasmic domain" or "cytoplasmic portion" as used herein are interchangeable and refer to the entire cytoplasmic domain or a portion of the cytoplasmic domain of a polypeptide or protein of interest. The invention is not limited solely to the cytoplasmic domains of polypeptides or proteins of interest that are fused to a PTD; in fact, other domains or portions of the polypeptides or proteins of interest may also be fused to a PTD.

As used herein, the term "polypeptide" is intended to encompass a singular "polypeptide" as well as plural "polypeptides," and comprises any chain or chains of two or more amino acids joined together by peptide bonds. Thus, as used herein, terms including, but not limited to "peptide," "dipeptide," "tripeptide," "protein," "amino acid chain," "oligopeptide," "oligomer," or any other term used to refer to a chain or chains of two or more amino acids, are included in the definition of a "polypeptide," and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids. The term "protein" is also intended to include fragments, analogues and derivatives of a protein wherein the fragment, analogue or derivative retains essentially the same biological activity or function as a reference protein.

The "fragment, derivative or analogue" of the protein may be (i) one in which one or more of the amino acid residues are substituted with a conserved or non-conserved amino acid residue (preferably, a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half life of the polypeptide (for example, polyethylene glycol); or (iv) one in which the additional amino acids are fused to the mature polypeptide, such as a leader or secretory sequence which is employed for purification of the polypeptide. Such fragments, derivatives and analogues are deemed to be within the scope of those skilled in the art from the teachings herein.

Particularly preferred are variants, analogues, derivatives and fragments having the amino acid sequence of the protein in which several, e.g., 5 to 10, 1 to 5, 1 to 3, 2, or 1 amino acid residues are substituted, deleted or added in any combination. Especially preferred among these are silent substitutions, additions and deletions, which do not alter the properties and activities of the protein of the present invention. Also especially preferred in this regard are conservative substitutions.

An example of a variant of the present invention is a fusion protein as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

The terms "biomolecule transduction complex" or BTC, refer to a complex of a PTD and a molecule of interest. The molecule of interest can be a protein, a nucleic acid, a lipid, a carbohydrate or a chemical compound. If the molecule of interest is a protein, the BTC is also referred to as a fusion protein or fusion polypeptide.

The terms "fusion protein," "fusion polypeptide," "chimeric protein," and "chimeric polypeptide" as used herein are interchangeable and refer to polypeptides and proteins which comprise a polypeptide or protein of interest and a PTD.

The terms "protein of interest", "desired polypeptide", "desired protein" or "target protein" as used herein are interchangeable and refer to a whole protein molecule or a portion thereof, i.e., cytoplasmic domain or other domain of a protein. The cytoplasmic domain or other portion of the polypeptide or protein is capable of inducing a cellular response.

As used herein, the term "therapeutic agent" refers to a molecule, such as a protein, lipid, carbohydrate, nucleic acid or chemical compound, which when delivered to a vertebrate, treats, i.e., cures, ameliorates, or lessens the symptoms of, a given disease or condition (e.g., graft rejection) in that vertebrate, or alternatively, prolongs the life of the vertebrate by slowing the progress of a terminal disease or condition.

As used herein, the term "therapeutic fusion polypeptide" refers to a polypeptide which when delivered to a vertebrate, treats, i.e., cures, ameliorates, or lessens the symptoms of, a given disease or condition (e.g., graft rejection) in that vertebrate, or alternatively, prolongs the life of the vertebrate by slowing the progress of a terminal disease or condition.

Polypeptides

Therapeutic polypeptides of the present invention include, but are not limited to, cytokines, chemokines, lymphokines, ligands, receptors, hormones, apoptosis-inducing polypeptides, enzymes, antibodies, and growth factors. Examples include, but are not limited to the cytoplasmic domain of cytotoxic T-lymphocyte-associated protein 4 (ctCTLA-4), the cytoplasmic domain of zA1A2, granulocyte macrophage colony stimulating factor (GM-CSF), granulocyte colony stimulating factor (G-CSF), macrophage colony stimulating factor (M-CSF), colony stimulating factor (CSF), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFN™), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), *Leishmania* elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), erythropoietin (EPO), and insulin.

Therapeutic fusion polypeptides of the present invention may be used to treat diseases such as Parkinson's disease, cancer, and heart disease. In addition, therapeutic polypeptides may be used to treat autoimmune disorders such as multiple sclerosis; Sjogren's syndrome; sarcoidosis; insulin dependent diabetes mellitus; autoimmune thyroiditis; arthritis, e.g., osteoarthritis, rheumatoid arthritis, reactive arthritis, and psoriatic arthritis; ankylosing spondylitis; and scleroderma. Also, therapeutic polypeptides of the present invention can be used to treat acute and chronic inflammatory disorders (e.g., asthma), to promote wound healing, and to prevent graft rejection after transplantation of cells, tissues, or organs (e.g., islet transplantation).

Therapeutic fusion polypeptides of the present invention, for example, neurotrophic factors (NTFs), may be used to promote the survival, maintenance, differentiation, repair, regeneration, and growth of cells in the brain, spinal cord, and peripheral nerves. Suitable NTFs include, but are not limited to, NGF, BDNF, the Neurotrophins or NTs such as NT-2, NT-3, NT-4, NT-5, GDNF, CNTF, as well as others. The administration of purified recombinant NTFs represents a clinical strategy for treatment of such acute and chronic nervous system disorders. Such disorders include, but are not limited to mechanical or chemical brain or spinal cord injury, Parkinson's Disease, Alzheimer's Disease and other dementias, Amyotrophic Lateral Sclerosis and Multiple Sclerosis.

Therapeutic fusion polypeptides of the present invention, for example, growth factors, may be used to promote wound healing. Useful growth factors include, but are not limited to FGF and EGF.

Therapeutic fusion polypeptides of the present invention may be used to promote cell suicide (termed "apoptosis"). Suitable apoptotic polypeptides include the BAX protein. Alternatively, therapeutic fusion polypeptides of the present invention may be used to prevent apoptosis. Suitable apoptosis antagonists include the BAX antagonist Bcl-2. A disease which may be treated with apoptosis-inhibiting polypeptides is Muscular Dystrophy (MD), where patients have a defective protein called Dystrophin. Dystrophin is required for proper muscle function. The non-defective, normal Dystrophin may act as an antigen if delivered via plasmid DNA to patients with MD. In this case, muscle cells transduced with DNA encoding normal Dystrophin would be recognized by the immune system and killed by Dystrophin-specific T cell based responses. Such T cell based killing is known to kill cells by inducing apoptosis. If the normal, and potentially immunogenic, Dystrophin could be delivered into muscle cells along with Bcl-2 or other apoptosis-preventing protein, one would expect that CTL would be unable to kill the muscle cells. This reasoning applies to many genetic diseases where treatment involves delivery of a "normal", and therefore potentially immunogenic, copy of a protein.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides, which are used to prevent or treat, i.e., cure, ameliorate, lessen the severity of, or prevent or reduce diseases.

Further embodiments of the invention include polypeptides, which comprise amino acid sequences at least 95% identical, and more preferably at least 96%, 97%, 98% or 99% identical, to any of the amino acid sequences of the polypeptides described above.

As a practical matter, whether any particular polypeptide is at least 95%, 96%, 97%, 98% or 99% identical to, for instance, the amino acid sequence shown in SEQ ID NOs:11-18 can be determined conventionally using known computer programs such as the Bestfit program (Wisconsin Sequence Analysis Package, Version 8 for Unix, Genetics Computer Group, University Research Park 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acids in the reference sequence are allowed.

Polynucleotides

Additionally, the present invention relates to polynucleotides which encode fusion proteins or chimeric proteins, recombinant expression vectors, plasmids and other polynucleotide constructs (collectively referred to as "expression vectors") containing the same, microorganisms transformed with these expression vectors, and processes for obtaining these polynucleotides, and transformed cells using said vectors. Suitable host cells can be transformed with the expression vectors.

As used herein, the term "expression vector" refers to a construct made up of genetic material (i.e., nucleic acids). Typically, a expression vector contains an origin of replication which is functional in bacterial host cells, e.g., *Escherichia coli*, and selectable markers for detecting bacterial host cells comprising the expression vector. Expression vectors of the present invention contain a promoter sequence and include genetic elements as described herein arranged such that an inserted coding sequence can be transcribed and translated in eukaryotic cells. In certain embodiments described herein, an expression vector is a closed circular DNA molecule.

The term "expression" refers to the biological production of a product encoded by a coding sequence. In most cases, a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The fusion proteins or chimeric proteins of this invention can be prepared by recombinant DNA methodology. In accordance with the present invention, a gene sequence coding for a desired protein is isolated, synthesized or otherwise obtained and operably linked to a DNA sequence coding for the PTD peptide. The hybrid gene containing the gene for a desired protein operably linked to a DNA sequence encoding a PTD peptide is referred to as a chimeric gene. Optionally, the gene sequence coding for a desired protein may be operably linked to the DNA sequence coding for the PTD peptide via a linker peptide.

The term "linker peptide" is intended to define any sequence of amino acid residues which preferably provide a hydrophilic region when contained in an expressed protein. Such a hydrophilic region may facilitate cleavage by an enzyme at the proteolytic cleavage site.

The chimeric gene is inserted into an expression vector which allows for the expression of the desired chimeric protein in a suitable transformed host. The expression vector provides the inserted chimeric gene with the necessary regulatory sequences to control expression in the suitable transformed host.

The nucleic acid construct may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

Regulatory elements that control expression of the fusion protein of the present invention include the promoter region, the 5' untranslated region, the signal sequence, the chimeric coding sequence, the 3' untranslated region, and the transcription termination site. Fusion proteins which are to be secreted from a host into the medium also contain the signal sequence.

Similarly, a variety of translation control elements are known to those of ordinary skill in the art. These include, but are not limited to ribosome binding sites, and translation initiation and termination codons.

Methods and materials for preparing recombinant vectors and transforming host cells using the same, replicating the vectors in host cells and expressing biologically active foreign polypeptides and proteins are described in Principles of Gene Manipulation, by Old and Primrose, 2nd edition (1981), and Sambrook et al., Molecular Cloning, 3$^{rd}$ edition, Cold Spring Harbor Laboratory (2001), both incorporated herein by reference.

As used herein, the term "DNA polynucleotide" may be a circular or linearized plasmid, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Cherng, J. Y., et al., *J. Control. Release* 60:343-53 (1999), and Chen, Z. Y., et al., *Mol. Ther.* 3:403-10 (2001), both of which are incorporated herein by reference.

Further embodiments of the invention include vectors comprising chimeric genes, which comprise a nucleotide sequence at least 95% identical, and more preferably at least 96%, 97%, 98% or 99% identical, to any of the nucleotide sequences of the vectors comprising chimeric genes described above.

Other embodiments of the invention include chimeric genes, which comprise a nucleotide sequence at least 95% identical, and more preferably at least 96%, 97%, 98% or 99% identical, to any of the nucleotide sequences of the chimeric genes described above.

As a practical matter, whether any particular vector or chimeric gene is at least 95%, 96%, 97%, 98% or 99% identical to a nucleotide sequence according to the present invention, can be determined conventionally using known computer programs such as the Bestfit program (Wisconsin Sequence Analysis Package, Version 8 for Unix, Genetics Computer Group, University Research Park 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Codon Optimization

"Codon optimization" is defined as modifying a nucleic acid sequence for enhanced expression in the cells of the vertebrate of interest, e.g., human, by replacing at least one, more than one, or a significant number, of codons of the native sequence with codons that are more frequently or most frequently used in the genes of that vertebrate. Various species exhibit particular bias for certain codons of a particular amino acid.

In one aspect, the present invention relates to polynucleotide expression constructs or vectors, and host cells comprising nucleic acid fragments of codon-optimized coding regions which encode therapeutic polypeptides, and fragments, variants, or derivatives thereof, and various methods of using the polynucleotide expression constructs, vectors, host cells to treat or prevent disease in a vertebrate.

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). Many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Consensus Sequences

The present invention is further directed to expression plasmids that contain chimeric genes which express therapeutic fusion proteins with specific consensus sequences, and fragments, derivatives and variants thereof. A "consensus sequence" is, e.g., an idealized sequence that represents the amino acids most often present at each position of two or more sequences which have been compared to each other. A consensus sequence is a theoretical representative amino acid sequence in which each amino acid is the one which occurs most frequently at that site in the different sequences which occur in nature. The term also refers to an actual sequence which approximates the theoretical consensus. A consensus sequence can be derived from sequences which have, e.g., shared functional or structural purposes. It can be defined by aligning as many known examples of a particular structural or functional domain as possible to maximize the homology. A sequence is generally accepted as a consensus when each particular amino acid is reasonably predominant at its position, and most of the sequences which form the basis of the comparison are related to the consensus by rather few substitutions, e.g., from 0 to about 100 substitutions. In general, the wild-type comparison sequences are at least about 50%, 75%, 80%, 90%, 95%, 96%, 97%, 98% or 99% identical to the consensus sequence. Accordingly, polypeptides of the invention are about 50%, 75%, 80%, 85%, 90%, 91%, 92%, 93%, 94%, 95%, 96%, 97%, 98%, 99% or 100% identical to the consensus sequence.

A "consensus amino acid" is an amino acid chosen to occupy a given position in the consensus protein. A system which is organized to select consensus amino acids can be a computer program, or a combination of one or more computer programs with "by hand" analysis and calculation. When a consensus amino acid is obtained for each position of the aligned amino acid sequences, then these consensus amino acids are "lined up" to obtain the amino acid sequence of the consensus protein.

Therapeutic Uses

Contemplated is the use of the therapeutic fusion proteins in the manufacture of a medicament for the treatment of inflammatory and immune disorders, such as asthma, rheumatoid arthritis, hay fever, allergic rhinitis, psoriasis and other dermatoses, as well as to suppress graft rejection, e.g., in islet transplantation.

Further contemplated is the use of the therapeutic fusion proteins to modulate the immune response, i.e., to block T cell activation in subjects suffering from autoimmune disease, reduce the infiltration of inflammatory cells (airway inflammation), reduce the secretion of Th2 type cytokines, or reduce airway hyper-responsiveness. Examples of autoimmune disorders include multiple sclerosis; Sjogren's syndrome; sarcoidosis; insulin dependent diabetes mellitus; autoimmune thyroiditis; arthritis, e.g., osteoarthritis, rheumatoid arthritis, reactive arthritis, and psoriatic arthritis; ankylosing spondylitis; and scleroderma.

Also contemplated is the use of the therapeutic fusion proteins for the treatment of inflammatory disorders, such as asthma, emphysema, hay fever (atopy), allergic rhinitis, psoriasis and other dermatoses, as well as to suppress graft rejection, e.g., in islet transplantation.

Methods and Administration

The present invention provides methods for delivery of a therapeutic fusion polypeptide or a fragment, variant, or derivative thereof, wherein the protein is provided as a recombinant protein, in particular, a fusion protein, or a purified subunit, which comprises administering to a vertebrate one or more of the compositions described herein; such that upon administration of compositions such as those described herein, a therapeutic response is generated in the vertebrate. The delivery can occur, for example, through the skin, nose, eye, or intra-tracheal. Intra-nasal administration may occur via intra-tracheal instillation.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The present invention further provides a method for generating, enhancing or modulating an immune response comprising administering to a human one or more of the compositions described herein. In this method, the compositions may include one or more polypeptides, or a fragment, variant, or derivative thereof, wherein the protein is provided as a recombinant protein, in particular, a fusion protein, or a purified subunit.

As used herein, a "therapeutic response" refers to the ability of a vertebrate to elicit a positive reaction to a composition, as disclosed herein, when delivered to that vertebrate. Examples of therapeutic responses include, but are not limited to, immune responses, wound healing, inflammatory responses, and suppression of graft rejection.

As used herein, an "immune response" refers to the ability of a vertebrate to elicit an immune reaction to a composition delivered to that vertebrate. Examples of immune responses include an antibody response or a cellular, e.g., cytotoxic T cell, response.

As mentioned above, compositions of the present invention can be used to therapeutically treat and prevent disease. As defined herein, "treatment" refers to the use of one or more compositions of the present invention to prevent, cure, retard, or reduce the severity of a disease or disease symptoms in a vertebrate, and/or result in no worsening of the disease.

The term "prevention" refers to the use of one or more compositions of the present invention to generate a therapeutic responses in a vertebrate. It is not required that any composition of the present invention totally cure or eliminate all disease symptoms.

In certain embodiments, one or more compositions of the present invention are delivered to a vertebrate by methods described herein, thereby achieving an effective therapeutic and/or an effective preventative immune response. More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the vertebrate from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944, both of which are incorporated herein by reference in their entireties.

In certain embodiments, the compositions are administered to muscle, either skeletal muscle or cardiac muscle, or to lung tissue.

According to the disclosed methods, compositions of the present invention can be administered by intramuscular (i.m.), subcutaneous (s.c.), or intrapulmonary routes. Other suitable routes of administration include, but are not limited to intratracheal instillation, transdermal, intraocular, intranasal, inhalation, intracavity, intravenous (i.v.), intraductal (e.g., into the pancreas) and intraparenchymal (i.e., into any tissue) administration. For intravenous administration, appropriate pharmaceutically acceptable carriers can be used, such as phosphate buffered saline, saline, or other materials used for administration of drugs intravenously. Transdermal delivery includes, but is not limited to intradermal (e.g., into the dermis or epidermis), transdermal (e.g., percutaneous) and transmucosal administration (i.e., into or through skin or mucosal tissue). Intracavity administration includes, but is not limited to administration into oral, vaginal, rectal, nasal, peritoneal, or intestinal cavities as well as, intrathecal (i.e., into the spinal canal), intraventricular (i.e., into the brain ventricles or the heart ventricles), intra atrial (i.e., into the heart atrium) and sub arachnoid (i.e., into the sub arachnoid spaces of the brain) administration.

Any mode of administration can be used so long as the mode results in delivery or the expression of the desired peptide or protein, in the desired tissue, in an amount sufficient to generate a therapeutic response to a disease condition in a human in need of such a response.

Administration means of the present invention include needle injection (for example as a sterile aqueous dispersion, preferably isotonic), catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15: 1908-1916 (1997)), Biojector (Davis, H., et al., *Vaccine* 12: 1503-1509 (1994); Gramzinski, R., et al., *Mol. Med.* 4: 109-118 (1998)), AdvantaJet (Linmayer, I., et al., *Diabetes Care* 9:294-297 (1986)), Medi-jector (Martins, J., and Roedl, E. J., *Occup. Med.* 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams or gels, and decanting, use of polynucleotide coated suture (Qin, Y., et al., *Life Sciences* 65: 2193-2203 (1999)) or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M., et al., *Proc. Natl. Acad. Sci USA* 96:4262-7 (1999); Hartikka, J., et al., *Mol. Ther.* 4:407-15 (2001); Mathiesen, I., *Gene Ther.* 6:508-14(1999); Rizzuto G., et al., *Hum. Gen. Ther.* 11:1891-900 (2000). Each of the references cited in this paragraph is incorporated herein by reference in its entirety.

Determining an effective amount of one or more compositions of the present invention depends upon a number of factors including, for example, the fusion polypeptide, variants, or derivatives thereof being expressed or administered directly, the age, weight and sex of the subject, the precise condition requiring treatment and its severity, the route of administration, the in vivo half-life of the fusion polypeptide, the efficiency of uptake, and the area to be treated. Treatment can be repeated as necessary, based on clinical judgment, in view of patient response.

A "pharmaceutically effective amount" or a "therapeutically effective amount" is an amount sufficient to generate a therapeutic or clinical response to a disease condition. The terms "pharmaceutically effective amount" or a "therapeutically effective amount are interchangeable. Based on the above factors, determining the precise amount, number of doses, and timing of doses are within the ordinary skill in the art and will be readily determined by the attending physician or veterinarian.

For administration to mammals, and particularly humans, it is expected that the daily dosage of the active agent will be from 0.01 mg/kg body weight, typically around 1 mg/kg. The above dosages are exemplary of the average case. There can, of course, be instances where higher or lower dosages are merited, including picomolar and nanomolar concentrations, and such are within the scope of this invention.

The present invention also relates to compositions comprising the fusion polypeptide(s), as disclosed herein, and an additional pharmaceutically active agent. Therefore, the fusion polypeptide(s) and associated pharmaceutically active agent may be employed in combination with the pharmaceutically acceptable carrier or carriers. Such carriers may include, but are not limited to, saline, buffered saline, dextrose, liposomes, water, glycerol, polyethylene glycol, ethanol and combinations thereof.

Compositions of the present invention may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995), both of which are incorporated herein by reference in their entireties. Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims. All references cited in the Examples are incorporated herein by reference in their entireties.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual*, 2nd Ed., Sambrook et al., ed., Cold Spring Harbor Laboratory Press: (1989); DNA Cloning, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); and in Ausubel et al., *Current Protocols in Molecular Biology*, John Wiley and Sons, Baltimore, Md. (1989). Each of the references cited in this paragraph is incorporated herein by reference in its entirety.

Gene Construction

Constructs of the present invention are constructed based on the sequence information provided herein or in the art utilizing standard molecular biology techniques.

Plasmid Vectors

Constructs of the invention are derived from the pRSET-B expression vector (Invitrogen). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6/V5-His, pVAXb1, and pZeoSV2 (available from Invitrogen, San Diego, Calif.), and plasmid pCI (available from Promega, Madison, Wis.).

The vector backbones described above are used to create expression vectors which express the fusion proteins described herein. An expression vector may contain an additional promoter. Thus, the vector backbones described herein may contain multiple expression cassettes which comprise a promoter and a microbial coding sequence including, inter alia, polynucleotides as described herein. The expression cassettes may encode the same or different polypeptides. Additionally, the expression cassettes may be in the same or opposite orientation relative to each other. As such transcription from each cassette may be in the same or opposition direction (i.e., 5' to 3' in both expression cassettes or, alternatively, 5' to 3' in one expression cassette and 3' to 5' in the other expression cassette).

Plasmid DNA Purification

Plasmid DNA may be transformed into competent cells of an appropriate *Escherichia coli* strain (including but not limited to the DH5α strain) and highly purified covalently closed circular plasmid DNA was isolated by a modified lysis procedure or purified using Giga columns from Qiagen (Valencia, Calif.) according to the kit instructions. All plasmid preparations were free of detectable chromosomal DNA, RNA and protein impurities based on gel analysis. Plasmids were ethanol precipitated and resuspended in an appropriate solution, e.g., 150 mM sodium. DNA was stored at −20 degrees C. until use. DNA was diluted in the desired salt solution at the desired molar concentration.

Plasmid Expression in Mammalian Cell Lines

The expression plasmids were analyzed in vitro by transfecting the plasmids into Hela cells or Jurkat T cells. Other well-characterized human cell lines can also be used, e.g. MRC-5 cells, ATCC Accession No. CCL-171 or human rhabdomyosarcoma cell line RD (ATCC CCL-136). The transfection was performed using cationic lipid-based transfection procedures well known to those of skill in the art. Other transfection procedures are well known in the art and may be used, for example electroporation and calcium chloride-mediated transfection (Graham F. L. and A. J. van der Eb, *Virology* 52:456-67 (1973)). Following transfection, cell lysates and culture supernatants of transfected cells were evaluated to compare relative levels of expression of antigen. The samples were assayed by western blots and ELISAs, using commercially available polyclonal and/or monoclonal antibodies to compare both the quality and the quantity of expressed antigen.

Analysis of T Cell Activation

Primary human $CD4^+$ T cells were purified from buffy coats from healthy donors. PBMC were isolated by density gradient centrifugation using Histopaque (Sigma). The lymphocyte layer was collected and $CD4^+$ T cells were isolated by MACS column using CD4 microbeads (Miltenyi Biotec) (Busch R., et al., *J. Immunol. Methods* 286:97-109 (2004)).

One million Jurkat (E6.1) cells or primary human $CD4^+$ T cells were treated with Hph-1-ctCTLA-4 for 1 hour, then washed with PBS and incubated with 0.25 µg of anti-CD28 mAb (Pharmingen) for 20 min at 4° C. The anti-CD28 mAb bound cells were further activated in 0.05 µg of anti-CD3 mAb (Pharmingen) coated plates for 20 hours. Each cell was stained with anti-CD69-PE and anti-CD25-FITC antibodies (Pharmingen) and analyzed by FACS calibur (Becton Dickinson). The supernatant in each well was analyzed for the level of secreted IL-2 by ELISA (R&D system).

OVA-Induced Allergic Asthma Model

Six-weeks-old male BALB/c mice (Charles River Technology) were maintained under pathogen-free conditions. The mice were kept at 22° C. and 20 to 50% humidity with a 12 hour light. The OVA-challenged mice were sensitized on day 1 and 14 by intraperitoneal injection of 100 µg OVA (Sigma) emulsified in 20 mg of aluminum hydroxide (Sigma) in a total volume of 200 µl. On days 15, 16, and 17 after the initial sensitization, the mice were challenged by intranasal instillation of 1.5 mg OVA dissolved in 0.1 ml of 10% glycerol endotoxin free PBS (Van Rijt L. S., et al., *Blood* 100: 3663-3671 (2002); Oh S. W., et al., *J. Immunol.* 168:1992-2000 (2002); and Zhang Y., et al., *Am. J. Respir. Crit. Care*

Med. 155:661-669 (1997)). In the case of CTLA-4 treatment, mice received 25 μg of Hph-1-ctCTLA-4 recombinant protein in 50 μl of 10% glycerol endotoxin free PBS 30 min before OVA challenge via intranasal route.

Analysis of Inflammation in Airway

Airway resistance was measured by one chamber plethysmography (ALL Medicus) and expressed as fold increase for each concentration of MCh (methacholine) compared with Penh values after PBS challenge. Penh vales are Respiratory system resistance (Rrs) values represented as frequency of breath per min. Two days after the last OVA challenge, the mice were sacrificed with intraperitoneal injection of pentobarbital sodium (100 mg/kg) and bronchoalveolar lavage (BAL) was performed by 4 times instillation of 1 ml phosphate buffered saline and gentle retrieval. Cell numbers were measured using a hemocytometer and differential cell counts were performed on slides prepared by cyto-centrifugation and Diff-Quick staining (Scientific Products). Immediately following BAL, trachea and left main lung were fixed with 4% paraformaldehyde in PBS and embedded in paraffin. The tissues were subjected to H & E (hematoxylin and eosin) staining to permit morphometric analysis.

The severity of peribronchial inflammation was graded semiquantitatively as previously described, as follows: 0, normal; 1, fewer cells; 2, a ring of inflammatory cells with one cell layer deep; 3, a ring of inflammatory cells with more than four cells deep (Myou S., et al., *J. Exp. Med.* 198:1573-1582 (2003); and Myou S., et al., *J. Immunol.* 171:4379-4384 (2003)).

The levels of eotaxin, IL-5 (BD Biosciences), IL-6 and IL-13 (R&D System) in the BAL fluid were measured with a quantitative sandwich enzyme-linked immunoassay method (ELISA). The lower limit of detection was approximately 15.6 pg/ml, respectively. Values below this limit were considered to be zero for statistical analysis. Inter- and intra-assay coefficients of variance were determined to be less than 10%.

Example 1

Production of Expression Vectors

Based on common structural and functional features between TAT and uptake-targeting sequences which direct proteins from the cytosol to the intracellular organelles, an Hph-1 protein transduction domain (PTD) of 11 amino acids (YARVRRRGPRR) (SEQ ID NO:1) was identified from human transcriptional factor Hph-1. The terms "Hph-1-PTD" and "Hph-1" refer to this 11 amino acid sequence and are interchangeable.

Generation of Hph-1-PTD-ctCTLA-4, Hph-1-PTD-β-gal, Hph-1-PTD-ctCTLA-4-eGFP, and the corresponding genes not fused with Hph-1-PTD, was accomplished by generating PCR fragments and inserting each PCR fragment into the pRSET-B vector (Invitrogen) (FIG. 1A).

Example 2

Preparation of the Recombinant Proteins

Site-directed mutagenesis was conducted to create the CTLA-4YF mutant. The fidelity of the reading frame was verified by sequencing. BL21 star (Novagen) transformed with each DNA construct was induced for 5 hours with 1 mM IPTG and sonicated in lysis buffer (6 M urea, 20 mM Tris-HCl, pH 8.0 and 500 mM NaCl). Lysates were clarified by centrifugation (20,000 r.p.m. for 30 min at 20° C.), adjusted to 10 mM imidazole (Tris-HCl, pH 8.0) and loaded on HisTrap chelating columns (Qiagen). Bound proteins were eluted with 50, 100, 250 mM or 3M imidazole in Tris-HCl buffer with >95% purity. The recombinant proteins contained in each fraction were desalted on PD-10 Sephadex G-25 (Amersham Pharmacia). The purified proteins were supplemented with 10% glycerol, aliquoted and flash-frozen at –80° C. (Becker-Hapak M., et al., *Methods* 24:247-256 (2001)).

Example 3

Analysis of the In Vitro and In Vivo Transduction Efficiency of Hph-1-PTD

After the Hph-1-β-gal construct was transduced into each cell line for 1 hour, the cells were washed with PBS and fixed immediately. Then, the fixed cells were incubated with X-Gal solution for 1-3 hours at 37° C. The mice tissue samples from the liver, kidney, heart, lung, spleen and brain were isolated at 12 hours after i.p. injection of Hph-1-β-gal, sectioned (in 10- and 50-μm sections), and assayed using an X-Gal staining kit (Roche) (Schwarze S. R., et al., *Science* 285:1569-1572 (1999)). The image was captured by fluorescence microscopy (Nikon). Transduction capacity of Hph-1-β-gal was also analyzed by western blot analysis. Equal numbers of cells were solubilized in SDS-PAGE sample buffer and the proteins were resolved on a 12% gel, and blotted onto PVDF, which was probed with monoclonal antibody (1:1,000) to β-gal (Cell Signaling). Bound antibody was detected using horseradish peroxidase-conjugated antibody to mouse IgG (1:5, 000), followed by enhanced chemiluminescence (Pierce). To monitor the localization of the Hph-1-PTD-eGFP fusion protein, Hela cells were incubated with 10 μM of Hph-1-eGFP fusion protein for 30 min and the fluorescence of eGFP was analyzed by confocal microscopy (Bio Rad).

Transduction efficiency of Hph-1-HA-ctCTLA-4 was analyzed by intracellular staining using HA-fluorescein mAb (Cell Signaling). After cells were permeablized by cytofix/cytoperm solution (Pharmingen) and incubated with HA-fluorescein mAb at 4° C. for 30 min. Intracellular fluorescence was determined by FACS calibur (Becton Dickinson).

Using the purified Hph-1-β-gal fusion protein or the control β-gal protein, transduction efficiency was analyzed by western blot analysis in Jurkat (E6.1) cells. As shown in FIG. 1B, 10 μM of Hph-1-β-gal was readily transduced into the cultured cells, first detected at 15 min, and nearly maximum intracellular concentration was reached within less than 60 min. The degradation of the transduced protein was not detected up to 120 min after transduction, whereas the control β-gal protein was not transduced into the cells even at 20 mM. The protein transduction property of Hph-1-PTD appeared to manifest itself in a concentration-dependent manner, and the transduction efficiency was reduced by 40% at 4° C. (FIG. 1B).

After determination of transduction kinetics and the optimal concentration for protein transduction with Hph-1-PTD in Jurkat T cells, the transduction efficiency of Hph-1-PTD was tested with various cell lines. As shown in FIG. 1C, nearly 100% of the cells became positive for β-gal enzyme activity after 1 hour incubation with differential transduction efficiency.

To monitor the intracellular localization of Hph-1-PTD fused protein in cells, HeLa cells were incubated with 10 μM of Hph-1-eGFP fusion protein for 30 min and the fluorescence of eGFP was analyzed by confocal microscopy (FIG. 1D). Hph-1-eGFP accumulated in the nucleus a few minutes after incubation and the internalized fusion protein was found in both the nuclei and the cytoplasm of the treated cells (FIG. 1C).

To determine whether the Hph-1-PTD facilitated protein delivery in vivo, the Hph-1-β-gal or control β-gal protein was intra-peritoneally injected into mice, and the liver, heart, kidney, lung, spleen and brain were isolated at 4-6 hours after injection. The entire organs and their thin sections were then analyzed for β-gal enzyme activity (FIG. 1E). All of the tissues isolated from the mice injected with Hph-1-β-gal showed strong and uniform β-gal activity even within the brain section, indicating that Hph-1-PTD can deliver a large protein across the blood brain barrier. In mice injected with the control protein, β-gal was not detected or sporadic weak staining was observed that was likely due to the transient nonspecific uptake of control β-gal protein by phagocytic cells (Schwarze S. R., et al., *Science* 285:1569-1572 (1999)).

Example 4

Local Administration of Hph-1-FITC

Skin: The skin of hairless mice was swept with acetone and the mixture of Hph-1-FITC and ointment was applied to the backs of the mice. After 2 hours, the skin samples of the mice were sectioned and analyzed for the presence of fluorescence by confocal microscopy.

Eye: Hph-1-FITC in PBS solution was dropped on the eyes of a rat, and at 30 and 120 min after administration, FITC fluorescence was examined in the frozen section of the eye by confocal microscopy.

Nasal: FITC conjugated Hph-1-FITC solution was delivered into trachea and lung by intra-tracheal instillation. After 30 min, the left main lung and trachea were excised, fixed with 4% paraformaldehyde in PBS and embedded in paraffin. The thin sections from paraffin blocks were analyzed by confocal microscopy.

In order to utilize Hph-1-PTD in protein therapy for the treatment of local diseases, we attempted an administration of FITC-labeled Hph-1-PTD through the skin, eye or the nasal airway (FIG. 2). The FITC conjugated Hph-1-PTD mixed with ointment was topically applied to the skin of hairless mice. The skin sample was subsequently analyzed for the presence of fluorescence by confocal microscopy (FIG. 2A). Strong FITC fluorescence was detected in dermis as well as epidermis when treated with Hph-1-PTD-FITC whereas the basal level of fluorescence was observed in the skin of the mice treated with control peptide.

In FIG. 2B, Hph-1-PTD-FITC in PBS was dropped on the eyes of a rat. At 30 and 120 min after topical administration on the eye, FITC fluorescence was examined in the frozen section of the eye by confocal microscopy. Hph-1-FITC was able to penetrate into the retina and ganglion cell layer through sclera whereas the eye sample treated with control peptide was not fluorescent. In the next step, FITC conjugated Hph-1-PTD was locally delivered into trachea and lung by intra-tracheal instillation (FIG. 2C). Hph-1-PTD-FITC was detected in microbronchi and the endothelial area of vessels in lung and penetrated into the basement membrane of the bronchus.

Taken together, these results clearly show that Hph-1-PTD is able to deliver a large protein to the cytoplasm as well as the nuclei of cells both in vitro and in vivo. Since the in vivo delivery of a large protein through various local administration routes was effective, this indicates that the combination of functional fusion protein with Hph-1-PTD would be useful as a therapeutic protein drug through local administration.

Example 5

Inhibition of T Cell Activation by Hph-1-PTD Fused with the Cytoplasmic Domain of CTLA-4

By taking advantage of the capacity of Hph-1-PTD to deliver a large target protein into the cells or organs in vivo through nasal airway, a fusion protein of Hph-1-PTD and the cytoplasmic domain of CTLA-4 (Hph-1-PTD-ctCTLA-4) was constructed as described in FIG. 3A, to be used for local suppression of the immune response in an asthma model. We constructed control proteins comprised of ctCTLA-4 without Hph-1-PTD and Hph-1-ctCTLA-4YF, in which two tyrosine residues essential for its negative function were mutated into phenylalanine. The transduction efficiency of Hph-1-ctCTLA-4 was tested in Jurkat T cells, which are known not to express CTLA-4 on the surface. These cells were treated with different concentrations of Hph-1-ctCTLA-4 for different periods of time, and both the transduction efficiency and kinetics were analyzed by intracellular staining. As shown in FIGS. 3B and 3C, the transduction of Hph-1-ctCTLA-4 into the cells was determined to be concentration-dependent and maximal levels of intracellular Hph-1-ctCTLA-4 were reached at 60 min after incubation while CTLA-4 without Hph-1-PTD was not delivered at all.

To examine whether the delivered Hph-1-ctCTLA-4 can inhibit T cell activation, Jurkat T cells or primary human $CD4^+$ T cells were treated with Hph-1-ctCTLA-4 and stimulated with anti-CD28 mAb and plate-bound anti-CD3 mAb. The levels of activation-induced surface proteins such as CD69 and CD25 were analyzed by FACS. As shown in FIGS. 3D and 3E, the induction of these surface marker proteins was significantly inhibited by the intracellular presence of Hph-1-ctCTLA-4. ctCTLA-4 in the absence of Hph-1-PTD or the Hph-1-ctCTLA-4YF mutant did not show any inhibition of induction of these surface markers. Both Jurkat T cells and primary human $CD4^+$ T cells readily produce substantial quantities of IL-2 in response to stimulation with anti-CD3 and anti-CD28 mAbs, and 10 nM of CsA (Cyclosporine A) or FK506 inhibited IL-2 secretion as expected. The intracellular delivery of Hph-1-ctCTLA-4 to Jurkat or human $CD4^+$ T cells was able to inhibit the induction of IL-2 secretion in a concentration dependent manner at picomolar range, and the level of inhibition by 10 pM of Hph-1-ctCTLA-4 was better or equivalent to that by 10 mM of CsA (FIGS. 3F and 3G). A comparable level of inhibition of T cell activation was achieved by 1000-fold lower concentration of Hph-1-ctCTLA-4 than that of CsA. The induction of tyrosine phosphorylation of various intracellular signaling mediators, including Zap70, ERK and JNK after TcR stimulation was markedly inhibited upon delivery of Hph-1-ctCTLA-4 into T cells as previously reported (Lee K. M., et al., *Science* 282:2263-2266 (1998); Lee K. M., et al., *J. Immunol.* 168:4420-4429 (2002); Calvo C. R., et al., *J. Exp. Med.* 186:1645-1653 (1997); Kwon H. J., et al., *J. Immunol.* 173:6645-6653 (2004); and Brunner M. C., et al., *J. Immunol.* 162:5813-5820 (1999)). However, neither ctCTLA-4 without Hph-1-PTD nor Hph-1-ctCTLA-4YF blocked IL-2 secretion. These results showed that (1) the delivery of the cytoplasmic domain of CTLA-4 by Hph-1-PTD effectively blocks T cell activation at 10 pM concentration; and (2) two tyrosine residues in the cytoplasmic domain of CTLA-4 are essential for its inhibitory function (Emma L. M., et al., *J. Immunol.* 164: 5319-5327 (2000); and Thompson C. B. & Allison J. P., *Immunity* 7:445-450 (1997)).

Example 6

Hph-1-ctCTLA-4 Inhibited OVA-Induced Airway Inflammation

To determine whether the Hph-1-ctCTLA-4-eGFP fusion protein can be efficiently delivered into the trachea and lung by intra-tracheal instillation in mice, cells in bronchoalveolar lavage (BAL) fluid were collected at 12 hours after the administration of Hph-1-ctCTLA-4-eGFP fusion protein via the nasal route, and their fluorescence was analyzed by FACS. As shown in FIGS. 4A and 4B, a significant number of BAL cells became positive for eGFP. The in vivo transduction efficiency of the Hph-1-ctCTLA-4-eGFP fusion protein through the nasal airway occurred in a dose-dependent manner, but only the basal level of fluorescence was detected in BAL cells from mice treated with ctCTLA-4-eGFP. The transduction of Hph-1-ctCTLA-4-eGFP fusion protein into the $CD3^+$ T cells in BAL fluid was further analyzed. The high level of eGFP was detected in the majority of $CD3^+$ T cells from mice nasally instilled with Hph-1-ctCTLA-4-eGFP (FIG. 4C). From histological analysis of lung tissue, the delivery of Hph-1-ctCTLA-4-eGFP was apparent (data not shown). These results demonstrate that the cytoplasmic domain of CTLA-4 can be effectively delivered into BAL cells through nasal airway by Hph-1-PTD.

To investigate whether the Hph-1-ctCTLA-4 protein delivered through nasal airway is capable of suppressing the development of bronchial asthma in vivo, a mouse model for asthma was generated by immunization and airway challenge with OVA. After OVA challenge, the number of inflammatory cells including eosinophils, macrophages and neutrophils, and lymphocytes in the BAL fluid were significantly increased. The intra-nasal pretreatment of these mice with 25 µg of Hph-1-ctCTLA-4 was shown to prevent against the infiltration of these inflammatory cells into the BAL fluid to the levels observed in the PBS-challenged control group. However, Hph-1-ctCTLA-4YF mutant did not show these inhibitory effects (FIG. 4D).

To evaluate the inhibitory effect of Hph-1-ctCTLA-4 on the secretion of OVA-induced inflammatory cytokines, we measured the level of chemokines, such as eotaxin, and Th2 cytokines including the IL-5, IL-6, IL-13 and Th1 cytokines (IFN-γ, TGF-β) in the BAL fluid of OVA-challenged mice (FIG. 4E). The OVA-challenge caused a substantial increase in secretion of all cytokines. The single pretreatment of OVA-challenged mice with 25 µg of Hph-1-ctCTLA-4 significantly inhibited the production of eotaxin and Th2 type cytokines, but was not found to affect the generation of IFN-γ and TGF-β. Consistent with the results in FIG. 4D, there was no inhibition of the production of these Th2 cell cytokines in mice receiving either CTLA4 lacking Hph-1 or Hph-1-ctCTLA-4YF. Inflammatory index in the lung was significantly reduced in the OVA-challenged mice pretreated with Hph-1-ctCTLA-4, but not with Hph-1-ctCTLA-4YF (FIG. 4F).

When the histological examination was performed with lung tissues, it was determined that OVA challenge induced the infiltration of inflammatory cells into the peribronchial tissues around the airways and pulmonary blood vessels. Many mucus containing epithelial cells were also noted (FIG. 4G). Inflammatory cells could not infiltrate through the mucus in mice treated with Hph-1-ctCTLA-4. Surprisingly, these in vitro and in vivo inhibitory effects of Hph-1-ctCTLA-4 were not observed upon the delivery of Hph-1-ctCTLA-4-YF. This clearly demonstrates that the inhibitory effects of Hph-1-ctCTLA-4 are completely specific to ctCTLA-4.

Sensitization with OVA caused the substantial enhancement of airway hyperresponsiveness as evaluated by higher index of enhanced pauses after inhalation of nebulized methacholine compared with mice receiving saline inhalation (FIG. 5). The level of OVA-induced hyper-responsiveness to methacholine was substantially attenuated by Hph-1-ctCTLA-4, but not by CTLA4 without Hph-1-PTD or Hph-1-ctCTLA-4YF.

Recently there were two reports that intraperitoneal administration of fusion proteins between Tat-PTD and a dominant negative form of the class IA PI3K regulatory subunit (TAT-dnp85) or Ras (TAT-dnRas) effectively attenuated antigen-induced airway infiltration of eosinophils, reduced Th2 cytokine concentrations in BALF and blocked airway hyper-responsiveness to methacholine (Myou S., et al., *J. Exp. Med.* 198:1573-1582 (2003); and Myou S., et al., *J. Immunol.* 171: 4379-4384 (2003)). In these reports the animal received i.p. injection of TAT-dnp85 (10 mg/kg) and TAT-dnRas (10 mg/kg) every 12 h from the first OVA sensitization phase. However, TAT-dnp85 and TAT-dnRas had no effect on neutrophil and macrophage migration into the airway after antigen challenge. In contrast to this result, the Hph-1-PTD-ctCTLA-4 of the present invention effectively inhibited both neutrophil and macrophage infiltration as well as other inflammatory cells, and this inhibitory effect was accomplished by single administration of only about 1 mg/kg of Hph-1-ctCTLA-4 through the nasal route right before the first OVA challenge phase.

We conclude that the nasal administration of the cytoplasmic domain of CTLA-4 using the novel Hph-1-PTD efficiently blocks allergic inflammation, the infiltration of inflammatory cells, such as neutrophils and eosinophils, and the secretion of Th2 type cytokines in antigen-sensitized mice. This treatment also appears to reduce airway hyper-responsiveness to methacholine.

Example 7

Inhibition of T Cell Activation by Tat-PTD Fused with the Cytoplasmic Domain of CTLA-4

To examine the inhibition of T cell activation by Tat-PTD fused with the cytoplasmic domain of CTLA-4 (Tat-PTD-ctCTLA-4), Jurkat T cells stimulated with anti-CD3 and anti-CD28 mAb were treated with Tat-PTD-ctCTLA-4, and the levels of secreted IL-2 were measured using the ELISA kit (BD Biosciences Cat. No. 555190). As disclosed herein, the terms "Tat-PTD-ctCTLA-4" and "Tat-ctCTLA-4" are interchangeable.

Jurkat T cells stimulated with anti-CD3 and anti-CD25 mAb were distributed at a density of $2 \times 10^5$ cells on 96-well plates and then each well was treated with the Tat-PTD-ctCTLA-4 at either 10 pM, 1 pM, or 0.1 pM. The plates were incubated overnight at 37° C.

The collected supernatants in each well were added to micro well plates which were coated with 4 ng/ml antibody against human IL-2, blocked for 1 hour at room temperature with PBS containing 10% PBS, and washed. Media was removed, and 1.6 ng/ml biotinylated antibody against human IL-2 and avidin-horseradish peroxidase conjugate were added for 1 hour. After the plate was washed with PBS containing 0.02% Tween-20, 100 µl of substrate solution was added for 30 min. To stop the reaction, 2N $H_2SO_4$ solution was added and the absorbance at 450 nm was measured (FIG. 6).

FIG. 6 shows that the intracellular delivery of Tat-ctCTLA-4 to Jurkat T cells was able to inhibit the induction of IL-2 secretion in a concentration dependent manner at picomolar range, and the level of inhibition by 1 pM of Tat-ctCTLA-4 was better or equivalent to that by 10 nM of Cyclosporine (FIG. 6). Thus, a comparable level of inhibition of T cell activation was achieved by 10,000-fold lower concentration of Tat-ctCTLA-4 than that of Cyclosporine.

Example 8

Mph-1-PTD-ctCTLA-4 for Rheumatoid Arthritis

The immunosuppressive effects of Mph-1-PTD-ctCTLA-4 were analyzed using the Rheumatoid Arthritis (RA) animal model induced by intraperitoneal injection of collagen type II.

The RA-induced mice were treated by intravenous injection of 4 µg or 400 ng/mouse of Mph-1-PTD-ctCTLA-4 everyday, and the Arthritis index concerning swelling of joints, TNF-α, and the number of $CD4^+$ and $CD8^+$ T cells were analyzed.

The mice, upon treatment, recovered from the inflammation. The Arthritis index and the level of TNF-α, which is an inflammatory cytokine (FIGS. 7 and 8, respectively), decreased whereas the number of $CD4^+$ and $CD8^+$ T cells in spleen and lung increased (FIG. 9). CIA is a negative control and represents mice with Collagen Induced Arthritis which were not treated with the therapeutic agent. MTS is a positive control and represents mice treated with methotrexate, a well known RA treatment substance.

Example 9

Method to Suppress Inflammation in Atopic Animals

Atopy can be considered as the canine equivalent of hay fever. Atopy is an autoimmune-disease where the $CD4^+$ lymphocytes of the Th2 type play a pivotal role in pathogenesis of the allergic disease. The present example shows a method to suppress inflammation in atopic animals by suppressing or inhibiting the expression of cytokines in T cells.

Male hairless rats (n=3/group, Jung-Ang Animal, Korea) were subjected to a magnesium-deficient diet. The rats were fed with Altromin (Lage, Germany), which is a standard maintenance diet low in magnesium, and supplied with deionized water. Generally, magnesium in serum fell to the lowest level by 15 days after the initiation of the diet, and onset of the disease was observed by 8±2 days. After 10 days, all animals showed intense erythema on the back and swelling of both ear lobes.

The Mph-1-ctCTLA4 application was started at day 11 of the diet. For topical administration, Mph-1-ctCTLA4 was dissolved in 5% glycerol solution.

The atopic dermatitis-induced rats were treated by transdermal administration of 500 µg/rat of Mph-1-ctCTLA4 three times a week for 3 weeks. Control animals were treated in the same way with the vehicle.

The clinical scores and TEWL (Transepidermal Water Loss) were analyzed and the suppression of inflammation in atopic animals was observed.

FIG. 11 shows that the dermatitis score was lower in rats treated with Mph-1-ctCTLA4. TEWL was also reduced in rats treated with Mph-1-ctCTLA4 as compared to control rats (see FIG. 12).

Example 10

Method to Suppress Graft Rejection in Islet Transplantation

Islets were isolated using the method of collagenase enzyme digestion and Ficoll purification from donors (Lewis rat). The isolated islets were transplanted into the liver via the portal vein of streptozotocin-induced diabetic rats (Fisher DM rat, Asan medical center).

The animals (n=3 rats/group) received daily intraperitoneal injection of PBS (negative control), 5 mg/kg cyclosporine, 4 µg/kg Mph-1-ctCTLA4, 40 µg/kg Mph-1-ctCTLA4 or 5 mg/kg Cyclosporine plus 4 µg/kg Mph-1-ctCTLA4 for 15 days.

Everyday, the glucose level in blood was measured. When the glucose level was 200 mg/dL, the animal was considered to be undergoing graft rejection. The results are shown in the Table below.

Graft survival after islet allograft (Lewis to Fisher) by Mph-1-ctCTLA4

| Group | Number | Mean survival days |
|---|---|---|
| Negative control | 3 | 5 ± 2 |
| Cyclosporine (5 mg/kg) | 3 | 6.8 ± 2.1 |
| Mph-1-ctCTLA4 (4 µg/kg) | 3 | 14.2 ± 6.5 |
| Mph-1-ctCTLA4 (40 µg/kg) | 3 | 82.5 ± 12.6 |
| Cyclosporine (5 mg/kg) + Mph-1-ctCTLA4 (4 µg/kg) | 3 | >100 |

Example 11

Inhibition of T Cell Activation by Hph-1-ζ-Chain

ζ chain is a 16-kDa molecule consisting of a very short extracellular domain, a transmembrane region, and a long cytoplasmic tail, which contains three immunoreceptor tyrosine-based activation motifs (ITAMs). It usually exists as a homodimer, so that there are six phosphorylation sites or ITAMs on the two ζ chains in the TCR complex. CD3 ζ functions as a transmembrane signaling molecule in T lymphocytes.

The conjugate with Hph-1 and ζ-chain was delivered into activated T cells and inhibited phosphorylation of ζ-chain because the conjugate competed against the ζ-chain which existed on the TcR complex.

To examine the inhibition of T cell activation by Hph-1-ζ-chain, Jurkat T cells stimulated with anti-CD3 and anti-CD28 mAb were treated with Hph-1-ζ-chain, and the levels of secreted IL-2 were measured using the ELISA kit (BD Biosciences Cat. No. 555190).

Jurkat T cells stimulated with anti-CD3 and anti-CD25 mAb were distributed at a density of $2 \times 10^5$ cells on 96-well plates and then each well was treated with the Hph-1-ζ-chain at 10 nM. The plates were incubated overnight at 37° C.

The collected supernatants in each well were added to micro well plates which were coated with 4 ng/ml antibody against human IL-2, blocked for 1 hour at room temperature with PBS containing 10% FBS, and washed. Media was removed, and 1.6 ng/ml biotinylated antibody against human IL-2 and avidin-horseradish peroxidase conjugate were added for 1 hour. After the plate was washed with PBS containing 0.02% Tween-20, 100 µl of substrate solution was added for 30 min. To stop the reaction, 2N H2SO4 solution was added and the absorbance at 450 nm was measured (FIG. 10).

FIG. 10 shows that the intracellular delivery of Hph-1-ζ-chain to Jurkat T cells was able to inhibit the induction of IL-2 secretion at nanomolar range.

What is claimed is:

1. A method for treating a mammal suffering from rheumatoid arthritis, comprising administering to said mammal a therapeutically effective amount of a fusion polypeptide comprising a protein transduction domain (PTD) and the cytoplasmic domain of CTLA-4 (SEQ ID NO: 11), wherein the PTD comprises an amino acid sequence selected from the group consisting of SEQ ID NOs: 2-10.

2. The method of claim 1, wherein the protein transduction domain comprises the amino acid sequence of SEQ ID NO:2.

3. The method of claim 1, wherein the protein transduction domain comprises an amino acid sequence selected from the group consisting of:
   (i) SEQ ID NO:2;
   (ii) SEQ ID NO:4;
   (iii) SEQ ID NO:5;
   (iv) SEQ ID NO:6; and
   (v) SEQ ID NO:8.

4. The method of claim 1, wherein the fusion polypeptide is applied in picomolar concentration.

5. The method of claim 1, wherein the fusion polypeptide is administered intravenously.

6. A method for treating a mammal suffering from rheumatoid arthritis, comprising administering to said mammal a therapeutically effective amount of a fusion polypeptide comprising a protein transduction domain (PTD) and a cytoplasmic domain of a receptor protein, wherein the PTD comprises an amino acid sequence selected from the group consisting of SEQ ID NOs: 2-10, wherein the cytoplasmic domain of the receptor protein is at least 95% identical to the amino acid sequence of SEQ ID NO:11, and wherein the cytoplasmic domain of the receptor protein inhibits T cell activation.

7. The method of claim 6, wherein the cytoplasmic domain of the receptor protein is at least 97% identical to the amino acid sequence of SEQ ID NO:11.

8. The method of claim 1, wherein the PTD comprises an amino acid sequence selected from the group consisting of SEQ ID NO:3, SEQ ID NO:7, SEQ ID NO:9, and SEQ ID NO:10.

9. The method of claim 8, wherein the therapeutically effective amount is an amount from about 400 ng/kg/day to about 4 µg/kg/day.

10. The method of claim 8, wherein the therapeutically effective amount is an amount sufficient to decrease Arthritis index and level of TNF-α.

11. The method of claim 6, wherein said cytoplasmic domain of CTLA-4 consists of the amino acid sequence of SEQ ID NO:11.

* * * * *

SEQUENCE LISTING

<160> NUMBER OF SEQ ID NOS: 19

<210> SEQ ID NO 1
<211> LENGTH: 11
<212> TYPE: PRT
<213> ORGANISM: Homo sapiens

<400> SEQUENCE: 1

Tyr Ala Arg Val Arg Arg Arg Gly Pro Arg Arg
1               5                   10

<210> SEQ ID NO 2
<211> LENGTH: 11
<212> TYPE: PRT
<213> ORGANISM: Mouse

<400> SEQUENCE: 2

Tyr Ala Arg Val Arg Arg Arg Gly Pro Arg Arg
1               5                   10

<210> SEQ ID NO 3
<211> LENGTH: 9
<212> TYPE: PRT
<213> ORGANISM: Mouse

<400> SEQUENCE: 3

Ala Lys Ala Ala Arg Gln Ala Ala Arg
1               5

<210> SEQ ID NO 4
<211> LENGTH: 11
<212> TYPE: PRT
<213> ORGANISM: Mouse

<400> SEQUENCE: 4

Tyr Gly Arg Lys Lys Arg Arg Gln Arg Arg Arg
1               5                   10

<210> SEQ ID NO 5
<211> LENGTH: 16
<212> TYPE: PRT
<213> ORGANISM: Mouse

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 34
<212> TYPE: PRT
<213> ORGANISM: Mouse

<400> SEQUENCE: 6

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
                20                  25                  30

Val Glu

```
<210> SEQ ID NO 7
<211> LENGTH: 7
<212> TYPE: PRT
<213> ORGANISM: Mouse

<400> SEQUENCE: 7

Arg Arg Arg Arg Arg Arg Arg
1               5

<210> SEQ ID NO 8
<211> LENGTH: 26
<212> TYPE: PRT
<213> ORGANISM: Mouse

<400> SEQUENCE: 8

Ala Ala Val Ala Leu Leu Pro Ala Val Leu Leu Ala Leu Leu Ala Pro
1               5                   10                  15

Ala Ala Ala Asp Gln Asn Gln Leu Met Pro
            20                  25

<210> SEQ ID NO 9
<211> LENGTH: 21
<212> TYPE: PRT
<213> ORGANISM: Mouse

<400> SEQUENCE: 9

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 10
<211> LENGTH: 21
<212> TYPE: PRT
<213> ORGANISM: Mouse

<400> SEQUENCE: 10

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 11
<211> LENGTH: 36
<212> TYPE: PRT
<213> ORGANISM: Unknown
<220> FEATURE:
<223> OTHER INFORMATION: ctCTLA-4

<400> SEQUENCE: 11

Lys Met Leu Lys Lys Arg Ser Pro Leu Thr Thr Gly Val Tyr Val Lys
1               5                   10                  15

Met Pro Pro Thr Glu Pro Glu Cys Glu Lys Gln Phe Gln Pro Tyr Phe
            20                  25                  30

Ile Pro Ile Asn
        35

<210> SEQ ID NO 12
<211> LENGTH: 114
<212> TYPE: PRT
<213> ORGANISM: Unknown
<220> FEATURE:
```

-continued

<223> OTHER INFORMATION: y-chain

<400> SEQUENCE: 12

Phe Leu Arg Val Lys Phe Ser Arg Ser Ala Glu Pro Pro Ala Tyr Gln
1               5                   10                  15

Gln Gly Gln Asn Gln Leu Tyr Asn Glu Leu Asn Leu Gly Arg Arg Glu
            20                  25                  30

Glu Tyr Asp Val Leu Asp Lys Arg Arg Gly Arg Asp Pro Glu Met Gly
        35                  40                  45

Gly Lys Pro Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 13
<211> LENGTH: 34
<212> TYPE: PRT
<213> ORGANISM: Unknown
<220> FEATURE:
<223> OTHER INFORMATION: ITAM A

<400> SEQUENCE: 13

Asn Gln Leu Tyr Asn Glu Leu Asn Leu Gly Arg Arg Glu Glu Tyr Asp
1               5                   10                  15

Val Leu Asp Lys Arg Arg Gly Arg Asp Pro Glu Met Gly Gly Lys Pro
            20                  25                  30

Arg Arg

<210> SEQ ID NO 14
<211> LENGTH: 32
<212> TYPE: PRT
<213> ORGANISM: Unknown
<220> FEATURE:
<223> OTHER INFORMATION: ITAM B

<400> SEQUENCE: 14

Lys Asn Pro Gln Glu Gly Leu Tyr Asn Glu Leu Gln Lys Asp Lys Met
1               5                   10                  15

Ala Glu Ala Tyr Ser Glu Ile Gly Met Lys Gly Glu Arg Arg Arg Gly
            20                  25                  30

<210> SEQ ID NO 15
<211> LENGTH: 29
<212> TYPE: PRT
<213> ORGANISM: Unknown
<220> FEATURE:
<223> OTHER INFORMATION: ITAM C

<400> SEQUENCE: 15

Lys Gly His Asp Gly Leu Tyr Gln Gly Leu Ser Thr Ala Thr Lys Asp
1               5                   10                  15

Thr Tyr Asp Ala Leu His Met Gln Ala Leu Pro Pro Arg
            20                  25

<210> SEQ ID NO 16

<211> LENGTH: 95
<212> TYPE: PRT
<213> ORGANISM: Unknown
<220> FEATURE:
<223> OTHER INFORMATION: PD-1

<400> SEQUENCE: 16

Arg Ala Ala Arg Gly Thr Ile Gly Ala Arg Arg Thr Gly Gln Pro Leu
1               5                   10                  15

Lys Glu Asp Pro Ser Ala Val Pro Val Phe Ser Val Asp Tyr Gly Glu
            20                  25                  30

Leu Asp Phe Gln Trp Arg Glu Lys Thr Pro Glu Pro Pro Val Pro Cys
        35                  40                  45

Val Pro Glu Gln Thr Glu Tyr Ala Thr Ile Val Phe Pro Ser Gly Met
    50                  55                  60

Gly Thr Ser Ser Pro Ala Arg Arg Gly Ser Ala Asp Gly Pro Arg Ser
65                  70                  75                  80

Ala Gln Pro Leu Arg Pro Glu Asp Gly His Cys Ser Trp Pro Leu
                85                  90                  95

<210> SEQ ID NO 17
<211> LENGTH: 265
<212> TYPE: PRT
<213> ORGANISM: Unknown
<220> FEATURE:
<223> OTHER INFORMATION: eGFP

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser

```
                225                 230                 235                 240
Gly Arg Thr Gln Ile Ser Ser Ser Phe Glu Phe Cys Ser Arg Arg
                    245                 250                 255

Tyr Arg Gly Pro Gly Ile His Arg Ile
                260                 265

<210> SEQ ID NO 18
<211> LENGTH: 653
<212> TYPE: PRT
<213> ORGANISM: Unknown
<220> FEATURE:
<223> OTHER INFORMATION: beta-Gal

<400> SEQUENCE: 18

Met Glu Leu Trp Lys Ser Cys Ile Phe Leu Phe Leu Asn Phe Cys Ile
1               5                   10                  15

Gln Ser Glu Gly Ile Val Arg Thr Ser Tyr Gly Asn Trp Asn Ile Pro
            20                  25                  30

Lys Ile Gly Asp Arg Asn Ile Pro Ser Phe Leu Ile Asp Glu Ser Lys
        35                  40                  45

Asn Gln Phe Leu Leu Asp Gly Leu Pro Phe Arg Tyr Ile Ser Gly Ser
    50                  55                  60

Ile His Tyr Phe Arg Ile Pro Arg Asp Arg Trp Asp Glu Arg Leu Gly
65                  70                  75                  80

Lys Val Arg Ala Leu Gly Phe Asn Ala Ile Gln Tyr Tyr Ile Pro Trp
                85                  90                  95

Asn Met His Glu Leu Glu Glu Gly Asn His Asp Phe Ser Gly Leu Leu
            100                 105                 110

Asp Phe Ala Glu Phe Ser Met Met Ala Phe His Lys Tyr Gly Leu Trp
        115                 120                 125

Thr Ile Leu Arg Val Gly Pro Tyr Ile Cys Gly Glu Leu Glu Asn Gly
    130                 135                 140

Gly Leu Pro Trp Trp Leu Leu Asn Lys Asn Val Thr Lys Gln Arg Ser
145                 150                 155                 160

Ser Asp Arg Val Phe Thr Arg Glu Val Glu Asn Trp Phe Glu Ile Leu
                165                 170                 175

Leu Pro Arg Val Lys Pro Leu Leu Arg Lys Asn Gly Gly Pro Val Leu
            180                 185                 190

Met Leu Gln Ile Glu Asn Glu Tyr Gly Ser Tyr Asp Ala Cys Asp Gln
        195                 200                 205

Gln Tyr Leu Arg Phe Leu Arg Asp Leu Thr Arg Ser Leu Val Gly Asp
    210                 215                 220

Asp Val Leu Leu Phe Thr Thr Asp Gly Ser Ala Glu Ser Leu Leu Lys
225                 230                 235                 240

Cys Gly Thr Val Glu Gly Val Phe Pro Thr Val Asp Phe Gly Pro Thr
                245                 250                 255

Asp Asp Ala Lys Glu Ile Glu Asn Asn Phe Lys Leu Gln Arg Lys Phe
            260                 265                 270

Ala Pro Asn Gly Pro Leu Val Asn Ser Glu Tyr Tyr Pro Gly Trp Leu
        275                 280                 285

Val Leu Trp Gly Gln Lys Lys Gln Asn Leu Pro Ser Pro Gln Thr Ile
    290                 295                 300

Ile Asn Gly Ser Gln Thr Met Tyr Ser Leu Gly Ala Ser Phe Asn Tyr
305                 310                 315                 320

Tyr Met Ile His Gly Gly Thr Asn Phe Gly Phe Trp Asn Gly Ala Glu
```

```
                    325                 330                 335
Thr Glu Ala Pro Cys Ile Thr Ser Tyr Asp Tyr Asp Ala Pro Ile Ser
            340                 345                 350
Glu Ser Gly Asp Val Thr Thr Lys Tyr Leu Glu Ile Arg Lys Trp Ile
        355                 360                 365
Lys Gly Leu Thr Asp Trp Pro Thr Pro Leu Asp Val Pro Gly Asn
    370                 375                 380
Ser Pro Lys Gly Arg Phe Gly Lys Ile Lys Met Arg Leu Val His Ser
385                 390                 395                 400
Val Glu Lys Leu Lys Thr Leu Thr Ser Leu Gly Asp Pro Gly Asp Cys
                405                 410                 415
Val Glu Thr Asp Lys Pro Ile Ser Phe Glu Thr Leu Lys His Pro Leu
            420                 425                 430
Gly Leu Val Ala Tyr Gln Ala Lys Ile Asn Ser Cys Gly Asn Leu Thr
        435                 440                 445
Ile Pro Ser Phe Gly Asp Phe Val His Val Tyr Leu Asn Gly Lys Tyr
    450                 455                 460
Ile Asp Thr Leu Thr Arg Arg Tyr Tyr Asn Leu Thr Arg Asn Ser Val
465                 470                 475                 480
Ile Ile Glu Gly Cys Leu Glu Asn Glu Asn Arg Leu Phe Met Leu
                485                 490                 495
Val Glu Asn Gln Gly Arg Lys Thr Phe Glu Thr Ile Asn Asp Arg Lys
            500                 505                 510
Gly Ile Leu Ser Asp Val Phe Met Asn Gly Gln Ala Ile Gln Phe Trp
        515                 520                 525
Thr Gln Cys Gly Ile Lys Leu Pro Leu Gln Glu Asp Phe Tyr Phe Arg
    530                 535                 540
Lys Ala Met Arg Asn Asn Tyr Arg Lys Asn Val Lys Ser Asn Gln Lys
545                 550                 555                 560
Gln Gly Val Phe Ile Gly Ile Leu Ser Val Asp Ala Pro Thr Asp Thr
                565                 570                 575
Trp Leu Asp Thr Thr Gly Trp Gly Lys Gly Ile Ala Ile Val Asn Gly
            580                 585                 590
Arg Asn Phe Gly Arg Tyr Trp Pro Thr Lys Gly Pro Gln Met Thr Leu
        595                 600                 605
Tyr Ile Pro Ala Glu Phe Leu Lys Ile Gly Glu Asn Ser Val Met Met
    610                 615                 620
Val Glu Leu Glu Gly Ala Glu Glu Ala Cys Thr Ser Thr Ser Ser Cys
625                 630                 635                 640
Ile Ala Asp Phe Ile Asp His Pro Val Phe Asp Phe Gln
                645                 650

<210> SEQ ID NO 19
<211> LENGTH: 36
<212> TYPE: PRT
<213> ORGANISM: Unknown
<220> FEATURE:
<223> OTHER INFORMATION: ctCTLA-4YF

<400> SEQUENCE: 19

Lys Met Leu Lys Lys Arg Ser Pro Leu Thr Thr Gly Val Phe Val Lys
1               5                   10                  15
```

```
-continued

Met Pro Pro Thr Glu Pro Glu Cys Glu Lys Gln Phe Gln Pro Phe Phe
            20                  25                  30

Ile Pro Ile Asn
        35
```